US012076577B2
::::

(12) United States Patent
Lieber et al.

(10) Patent No.: US 12,076,577 B2
(45) Date of Patent: Sep. 3, 2024

(54) DEVICES AND METHODS FOR REPAIR OF A SELECTED BLOOD VESSEL OR PART THEREOF AND RAPID HEALING OF INJURED INTERNAL BODY CAVITY WALLS

(71) Applicant: Prometheus Therapeutics Inc., Miami Shores, FL (US)

(72) Inventors: Baruch B. Lieber, Aventura, FL (US); John A. Rose, Colorado Springs, CO (US)

(73) Assignee: Prometheus Therapeutics Inc., Miami Shores, FL (US)

( * ) Notice: Subject to any disclaimer, the term of this patent is extended or adjusted under 35 U.S.C. 154(b) by 30 days.

(21) Appl. No.: 17/543,304

(22) Filed: Dec. 6, 2021

(65) Prior Publication Data
US 2022/0266050 A1  Aug. 25, 2022

Related U.S. Application Data

(63) Continuation of application No. 15/976,199, filed on May 10, 2018, now Pat. No. 11,191,976.
(Continued)

(51) Int. Cl.
*A61N 5/06* (2006.01)
*A61B 1/00* (2006.01)
(Continued)

(52) U.S. Cl.
CPC ........ *A61N 5/0601* (2013.01); *A61B 1/00045* (2013.01); *A61B 1/00087* (2013.01);
(Continued)

(58) Field of Classification Search
CPC .................. A61N 5/0601; A61N 5/062; A61N 2005/0602; A61N 2005/0662;
(Continued)

(56) References Cited

U.S. PATENT DOCUMENTS 5,741,323 A   4/1998   Pathak et al.
5,997,570 A   12/1999  Ligtenberg et al.
(Continued)

FOREIGN PATENT DOCUMENTS

JP   H01170451 A   7/1989
JP   H04166145 A   6/1992
(Continued)

OTHER PUBLICATIONS

Office Action for Australian Application No. AU20180269378 dated Mar. 3, 2023, 4 pages.
(Continued)

*Primary Examiner* — Eugene T Wu
(74) *Attorney, Agent, or Firm* — Cooley LLP

(57) ABSTRACT

In some embodiments, an apparatus includes a catheter having a catheter body, a light emitter disposed at a distal end of the catheter body, and a fluid conduit coupleable to a source of fluid. The fluid conduit configured to discharge fluid from the source via the conduit and out a distal end of the catheter body. A spacing member is disposed at the distal end of the catheter body and can be moved between a collapsed configuration and an expanded configuration. In the expanded configuration, the spacing member is disposed about the light emitter. The spacing member is at least partially transmissive and/or transflective of light emitted from the light emitter. The apparatus configured to be inserted at least partially into a body lumen, to discharge fluid into the body lumen, and to emit light from the light emitter to illuminate an interior wall of the body lumen.

26 Claims, 24 Drawing Sheets

Related U.S. Application Data

(60) Provisional application No. 62/508,690, filed on May 19, 2017.

(51) Int. Cl.

| | | |
|---|---|---|
| *A61B 1/05* | (2006.01) | |
| *A61B 1/313* | (2006.01) | |
| *A61B 17/02* | (2006.01) | |
| *A61B 17/12* | (2006.01) | |
| *A61B 18/24* | (2006.01) | |
| *A61F 2/90* | (2013.01) | |
| *A61M 25/00* | (2006.01) | |
| *A61B 17/00* | (2006.01) | |
| *A61B 17/22* | (2006.01) | |
| *A61B 18/00* | (2006.01) | |
| *A61B 18/22* | (2006.01) | |
| *A61B 90/00* | (2016.01) | |
| *A61F 2/82* | (2013.01) | |

(52) U.S. Cl.
CPC .............. *A61B 1/05* (2013.01); *A61B 1/3137* (2013.01); *A61B 17/0218* (2013.01); *A61B 17/12113* (2013.01); *A61B 17/12168* (2013.01); *A61B 17/12172* (2013.01); *A61B 17/12181* (2013.01); *A61B 18/24* (2013.01); *A61F 2/90* (2013.01); *A61M 25/00* (2013.01); *A61N 5/062* (2013.01); *A61B 2017/00292* (2013.01); *A61B 2017/00557* (2013.01); *A61B 2017/00778* (2013.01); *A61B 2017/00907* (2013.01); *A61B 2017/0225* (2013.01); *A61B 17/12118* (2013.01); *A61B 17/12136* (2013.01); *A61B 17/12186* (2013.01); *A61B 2017/22067* (2013.01); *A61B 2018/00029* (2013.01); *A61B 2018/00404* (2013.01); *A61B 2018/00416* (2013.01); *A61B 2018/00589* (2013.01); *A61B 2018/00982* (2013.01); *A61B 2018/2238* (2013.01); *A61B 2018/2261* (2013.01); *A61B 90/361* (2016.02); *A61B 2217/007* (2013.01); *A61F 2002/823* (2013.01); *A61F 2002/826* (2013.01); *A61N 2005/0602* (2013.01); *A61N 2005/0659* (2013.01); *A61N 2005/0662* (2013.01)

(58) Field of Classification Search
CPC ............ A61N 2005/0659; A61B 18/24; A61B 17/12181; A61B 17/12172; A61B 17/0218; A61B 1/00087; A61B 1/05; A61B 1/3137; A61B 17/12113; A61B 17/12168; A61B 1/00045; A61B 2018/00416; A61B 2018/2261; A61B 2018/00589; A61B 2017/00778; A61B 2018/00404; A61B 2017/00292; A61B 2018/00982; A61B 2018/2238; A61B 2018/00029; A61B 17/12118; A61B 2017/00557; A61B 2017/00907; A61B 17/12186; A61B 90/361; A61B 2017/0225; A61B 2217/007; A61B 2017/22067; A61B 17/12136; A61B 17/0057; A61B 17/00234; A61M 25/00; A61F 2/90; A61F 2002/826; A61F 2002/823

See application file for complete search history.

(56) References Cited

U.S. PATENT DOCUMENTS

| | | | |
|---|---|---|---|
| 7,942,925 B2 | 5/2011 | Yodfat et al. | |
| 11,191,976 B2 | 12/2021 | Lieber et al. | |
| 2004/0010248 A1* | 1/2004 | Appling | A61B 18/24 606/15 |
| 2004/0230156 A1 | 11/2004 | Schreck et al. | |
| 2008/0027517 A1 | 1/2008 | Burwell et al. | |
| 2008/0033341 A1* | 2/2008 | Grad | A61M 25/00 604/20 |
| 2008/0269846 A1 | 10/2008 | Burwell et al. | |
| 2008/0292255 A1 | 11/2008 | Stevens et al. | |
| 2014/0228829 A1 | 8/2014 | Schmitt et al. | |
| 2015/0005693 A1* | 1/2015 | Gerrans | A61B 17/3205 604/20 |
| 2016/0213945 A1 | 7/2016 | Burwell et al. | |
| 2016/0249934 A1* | 9/2016 | Hewitt | A61B 17/12177 606/200 |
| 2017/0135699 A1 | 5/2017 | Wolf | |
| 2017/0209677 A1* | 7/2017 | Kang | A61M 29/00 |
| 2022/0039635 A1 | 2/2022 | Shia | |

FOREIGN PATENT DOCUMENTS

| | | |
|---|---|---|
| JP | 2000024001 A | 1/2000 |
| JP | 2015073705 A | 4/2015 |
| WO | WO-9600102 A1 | 1/1996 |
| WO | WO-2018213503 A1 | 11/2018 |

OTHER PUBLICATIONS

International Search Report and Written Opinion for International Application No. PCT/US2018/033047, mailed Aug. 31, 2018, 14 pages.

Notice of Reasons for Rejection for Japanese Application No. 2020-514141, mailed Feb. 22, 2022, 15 pages.

Office Action for European Application No. 18732188.0, mailed Nov. 25, 2020, 6 pages.

Office Action for U.S. Appl. No. 15/976,199, mailed Dec. 15, 2020, 8 pages.

Examination Report in EP Application No. 18732188.0, dated Aug. 29, 2022, 9 pages.

Office Action for Japanese Application No. JP2020514141 dated Dec. 14, 2022, 11 pages.

Invitation to Pay Additional Fees for International Application No. PCT/US2023/074511, dated Jan. 26, 2024, 2 pages.

Office Action for Australian Application No. AU20180269378, dated Feb. 27, 2024, 4 pages.

* cited by examiner

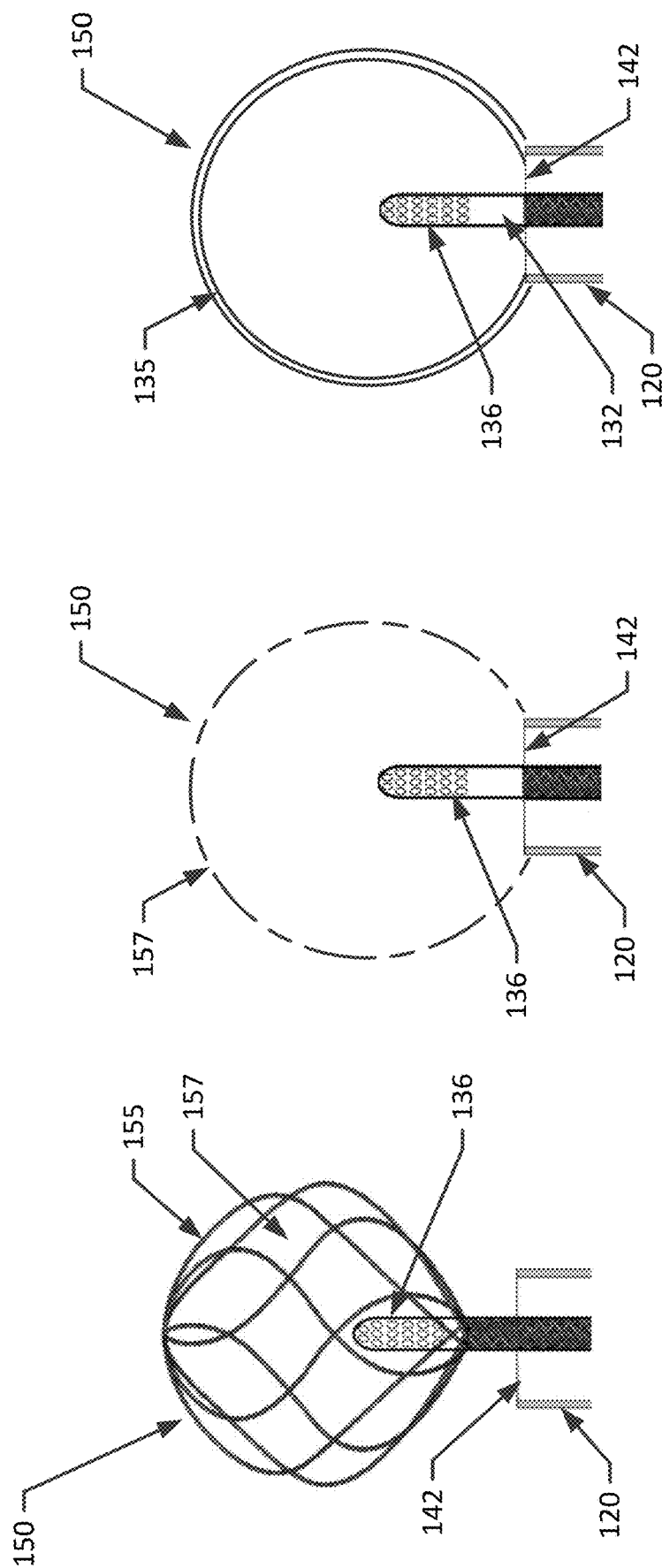

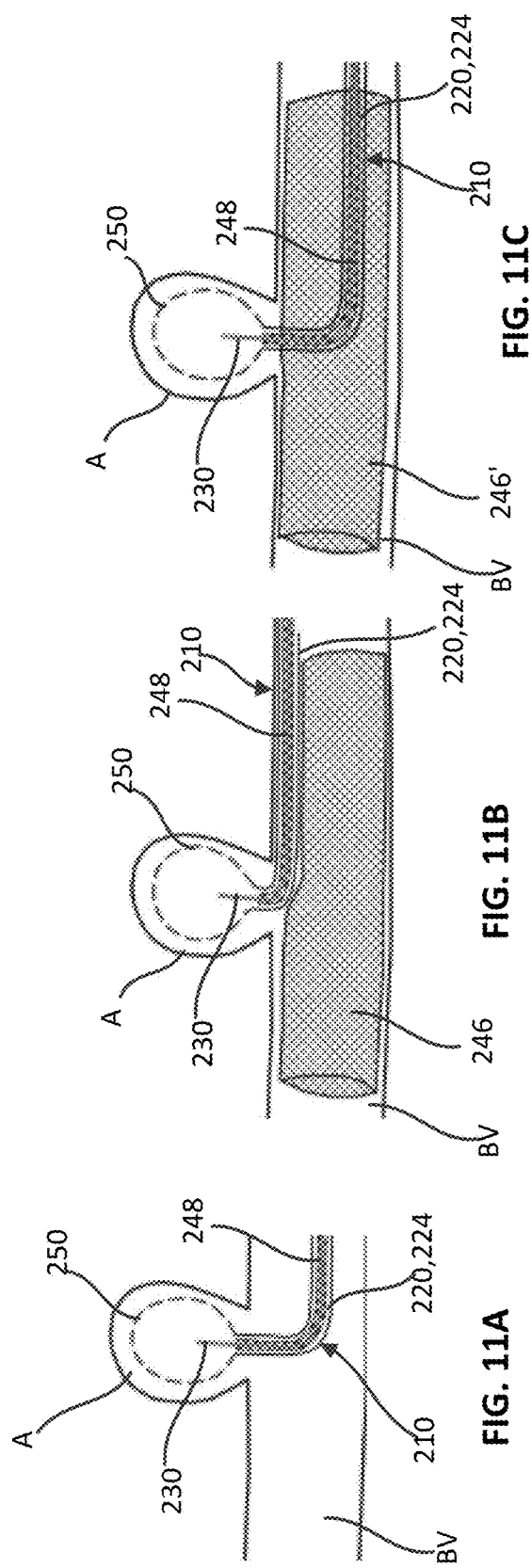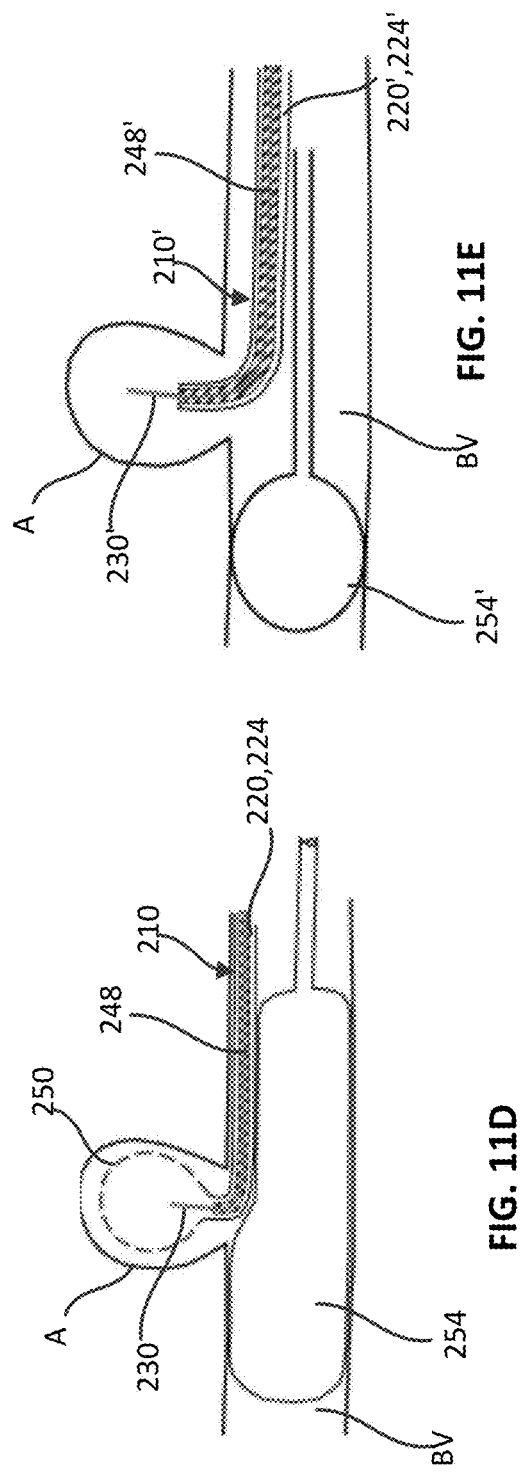

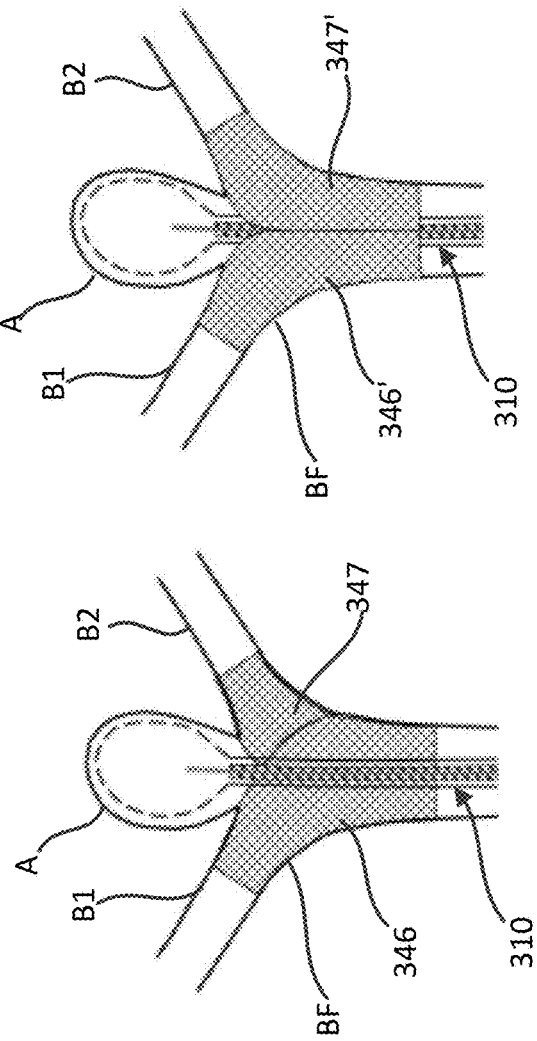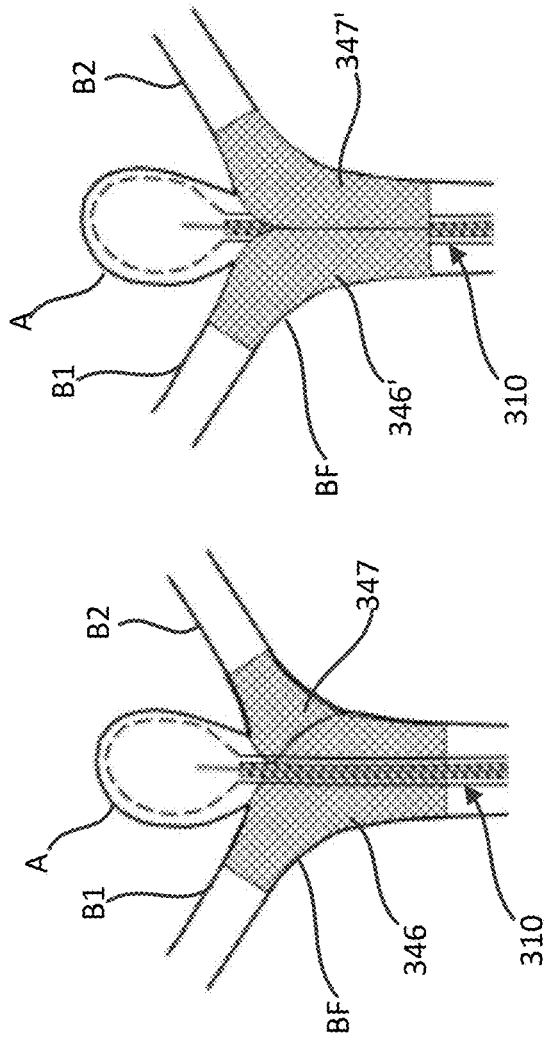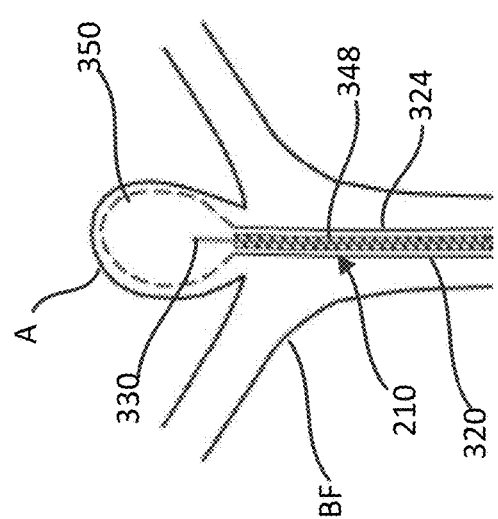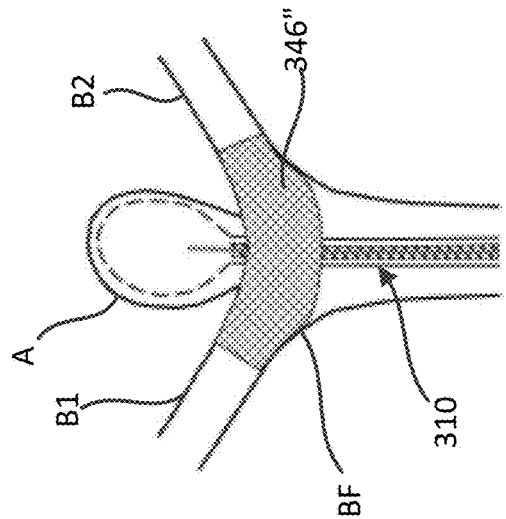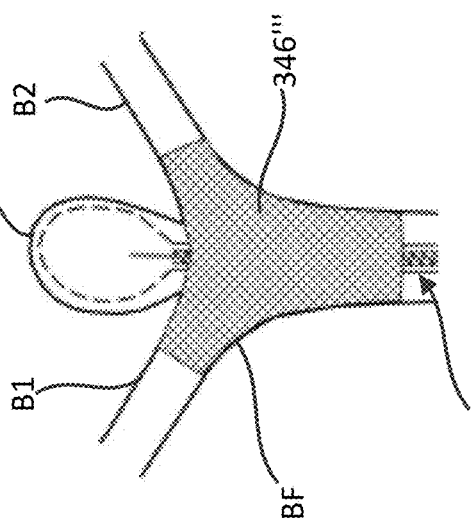

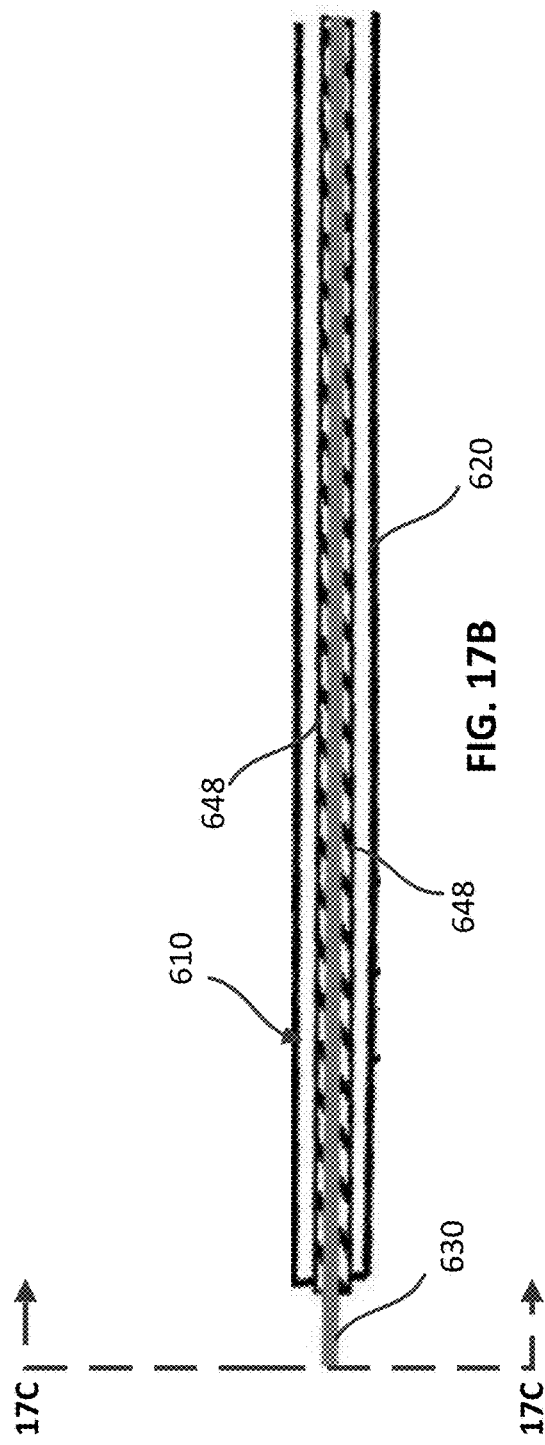
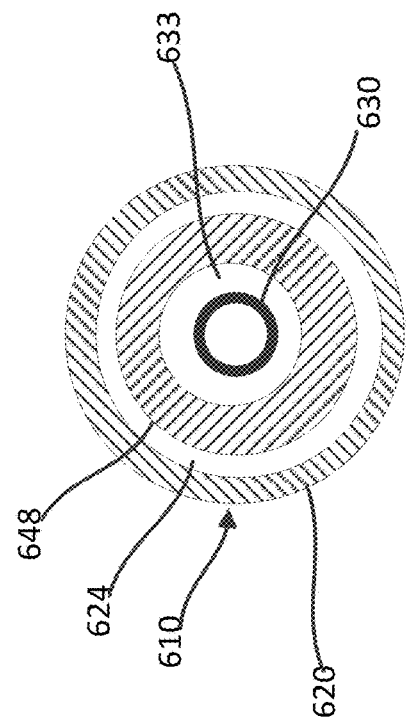

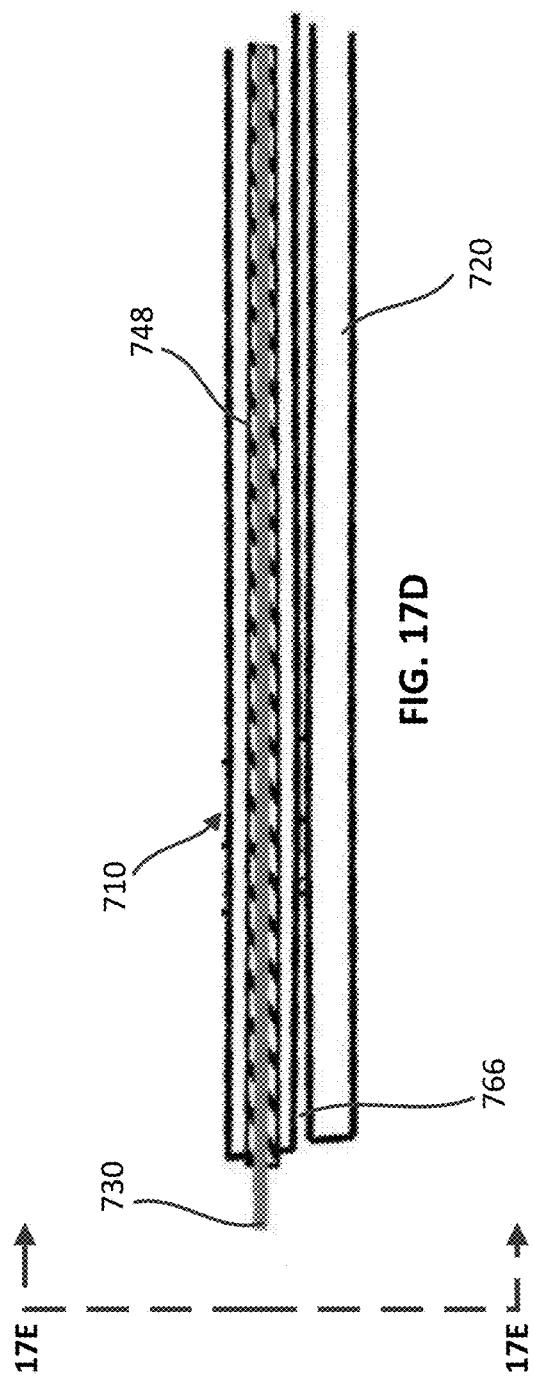
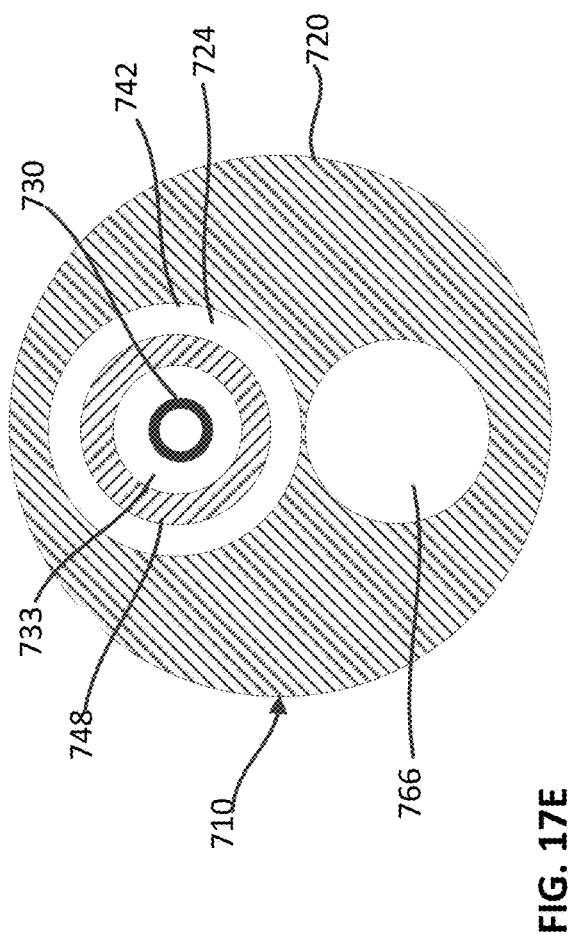
FIG. 17D
FIG. 17E

DEVICES AND METHODS FOR REPAIR OF A SELECTED BLOOD VESSEL OR PART THEREOF AND RAPID HEALING OF INJURED INTERNAL BODY CAVITY WALLS

CROSS-REFERENCE TO RELATED APPLICATIONS

This application is a continuation of U.S. patent application Ser. No. 15/976,199, filed May 10, 2018, now U.S. Pat. No. 11,191,976, which claims priority to and the benefit of U.S. Provisional Patent Application Ser. No. 62/508,690, entitled "Devices and Methods for Repair of a Selected Blood Vessel or Part Thereof and Rapid Healing of Injured Internal Body Cavity Walls," filed May 19, 2017, the disclosures of each of which is incorporated herein by reference in its entirety.

TECHNICAL FIELD

The present disclosure relates generally to systems, apparatus, and methods for therapeutic intervention in blood vessels and other body lumens or cavities.

BACKGROUND

The embodiments described herein relate generally to modulating blood flow (e.g. reduce flow rate or stop flow completely) to a selected blood vessel or part thereof.

Photothrombotic occlusion has been proposed as an approach to inducing permanent clotting in arteries. This approach involves intravenous or local introduction of a photosensitizer, such as sodium fluorescein, erythrosine B, or rose bengal dye, to be absorbed onto the endothelial luminal surface of the artery. A photochemical process is initiated by light at a wavelength sufficient to excite the molecules of the photosensitizer (e.g. 510 nm to 580 nm, or higher. e.g. 830 nm). This was believed to initiate a Type II photochemical process in which the energy of excitation is transferred to molecular oxygen, a metastable, highly reactive species. In turn, the singlet oxygen was believed to initiate direct peroxidation of unsaturated fatty acids and proteins in the luminal surface, leading to structural damage, which in turn stimulates platelet adherence, followed by platelet aggregation and occlusion of the vessel.

An alternative more recent mechanistic explanation of the observed photothrombosis process is that blood constituents such as multipotent stem cells and blood forming stem cells, as well as vascular wall constituents such as mesenchymal stem cells, vascular stem cells, and endothelial precursor cells, or progenitor cells, as well as differentiated cells such as fibroblasts and collagen are exposed to the effect of low level laser light that recruit cells locally and or remotely, initiate differentiation, activation and proliferation of the cells to produce the photothrombotic effect.

A technique used for treating an aneurysm is to deploy a permeable mesh-like tube of biocompatible material across the neck of the aneurysm to reduce blood flow into the aneurysm, activate the platelets passing through the device into the aneurysm, and thereby, promote coagulation of blood within the aneurysm.

One proposed approach to treatment of aneurysms and other malformations of blood vessels combines the photothrombotic and mesh-like tube approaches. In this approach, an optical fiber tip is deployed endovascularly into the aneurysm, preceded or followed by introduction of a mesh-like tube across the neck of the aneurysm. The tip applies light energy to the interior of the aneurysm to initiate or accelerate coagulation of blood in the aneurysm. A light-energy absorbing and/or transmission agent could also be introduced into the interior of the aneurysm before using the optical fiber to apply light energy.

One shortcoming of the proposed techniques is that the energy density of the light onto the wall of the blood vessel in the region to be treated (i.e. the energy per unit area of the vessel wall) cannot be well controlled to be relatively uniform, i.e. to be maintained within a range of energy density values that is high enough to be therapeutically effective and low enough not to damage the vessel wall.

Thus, there is a need for a device capable of more effectively treating aneurysms or other malformations, such as arteriovenous and dural malformations, in blood vessels, for devascularizing tumors, occluding varicose and spider veins, and treating other regions and indications by creating a stable thrombus in the region of interest.

SUMMARY

In some embodiments, an apparatus includes a catheter having a catheter body with a distal end and a proximal end. A light emitter is disposed at the distal end of the catheter body and configured to emit light. A fluid conduit is disposed in the catheter body, extending from the proximal end to the distal end of the catheter body, and has an inlet at the proximal end of the catheter body and is coupleable to a source of fluid, and has an outlet at the distal end and is configured to discharge fluid from the source via the conduit and out of the distal end. A spacing member is disposed at the distal end of the catheter body and reconfigurable from a collapsed configuration to an expanded configuration. In the expanded configuration, the spacing member is disposed about the light emitter to maintain the light emitter approximately centered within the spacing member with respect to at least one axis of the spacing member. The spacing member is at least partially transmissive and/or transflective of the light emitted from the light emitter. The apparatus is configured for the distal end of the catheter body to be inserted at least partially into a body lumen having an interior wall, for the spacing member to be disposed in the expanded configuration within the body lumen, for fluid to be discharged into the body lumen, and for light to be emitted from the light emitter to illuminate the interior wall of the body lumen.

BRIEF DESCRIPTION OF THE DRAWINGS

FIGS. 4A-4G are schematic illustrations of a spacing member of the system of FIG. 1.

FIGS. 11A-11E are schematic illustrations of devices and methods for treating an aneurysm in a blood vessel, according to embodiments.

FIGS. 12A-12E are schematic illustrations of devices and methods for treating an aneurysm at a bifurcation in a blood vessel, according to embodiments.

FIG. 17B is an enlarged side view of the device of FIG. 17A, and FIG. 17C is an end view of the device of FIG. 17B.

FIGS. 17D and 17E are side and end views, respectively, of an alternative embodiment of a device suitable for use in the method for treating a joint as shown in FIG. 17A.

DETAILED DESCRIPTION

Figure 1:
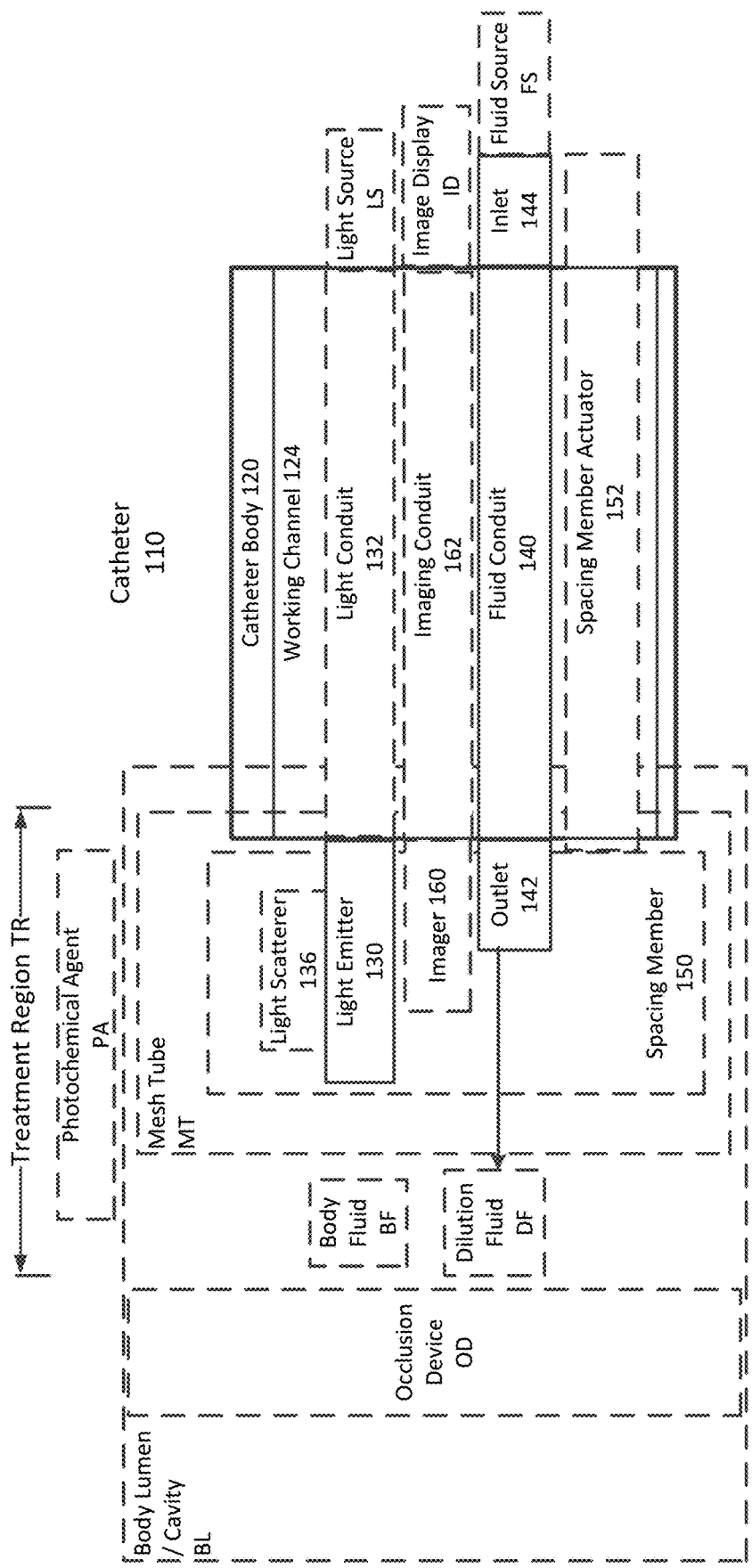
FIG. 1 is a schematic block diagram of a system, according to an embodiment.

Systems and methods are disclosed that are suitable for effectively treating blood vessels, including cerebral, coronary, and peripheral vessels, for aneurysms or other malformations (such as arteriovenous and dural malformations), as well as for blood vessel occlusion to devascularize tumors and to treat varicose and spider veins to exclude them from the circulation. The systems and methods may also be used for treating ulcerations in internal body cavity walls such as stomach ulcers, parenchymal tumors, such as brain tumors, liver tumors and other soft tissue non-vascular lesions of the body, bleeding vascular structures, arterial or venous (not by endovascular access), hemorrhoidal bleeding, esophageal varices, spider hemangiomas, bleeding of the joints, amyloid generative diseases, lymphangiomas, cartilage damage, joint inflammation such as rheumatoid arthritis, synovial joint inflammation and traumatic joint injury, bone repair, kidney tumor and inflammation disorders such as fibrosis, lungs Broncho-pulmonary system bleeding, myocardial injury, carotid disease, neurodegenerative disorders, and splenomegaly.

The disclosed system includes a catheter device that may include a catheter body with a distal end and a proximal end and a light emitter disposed at the distal end of the catheter body and configured to emit light. A fluid conduit is disposed in the catheter body, extending from the proximal end to the distal end of the catheter body. The fluid conduit has an inlet at the proximal end of the catheter body and is coupleable to a source of fluid, and has an outlet at the distal end and is configured to discharge fluid from the source via the conduit and out of the distal end. A spacing member is disposed at the distal end of the catheter body and is reconfigurable from a collapsed configuration to an expanded configuration. In the expanded configuration, the spacing member is disposed about the light emitter to maintain the light emitter approximately centered within the spacing member with respect to at least one axis of the spacing member. The spacing member is at least partially transmissive and/or transflective of the light emitted from the light emitter. The apparatus is configured for the distal end of the catheter body to be inserted at least partially into a body lumen having an interior wall, for the spacing member to be disposed in the expanded configuration within the body lumen, for fluid to be discharged into the body lumen, and for light to be emitted from the light emitter to illuminate the interior wall of the body lumen.

In some embodiments, a method includes disposing into a blood vessel of a subject adjacent to a region of a wall of the blood vessel to be treated, a distal end of a catheter. The distal end of the catheter is disposed at the center or proximal end of a treatment region. The catheter has disposed at the distal end thereof: a light emitter configured to emit light; an outlet of a fluid conduit coupled to a source of fluid; and a spacing member reconfigurable from a collapsed configuration to an expanded configuration. The spacing member can be at least partially transmissive and/or transflective of the light emitted from the light emitter, and porous to fluid discharged from the fluid outlet. The spacing member can be moved to the expanded configuration when disposed at the treatment location. When in the expanded configuration, the spacing member can be disposed about the light emitter to maintain the light emitter approximately centered within the spacing member with respect to at least one axis of the spacing member. The method further includes disposing the spacing member approximately centered within the blood vessel lumen. A fluid is discharged from the outlet of the fluid conduit into the blood vessel to dilute the blood in the blood vessel with the fluid. Light is emitted from the light emitter through the diluted blood in the blood vessel lumen and onto the region of the wall of the blood vessel to be treated.

As illustrated schematically in FIG. 1, a treatment system 100 can include a catheter 110, which may be operatively coupled to other devices or systems, including a light source LS, a fluid source FS, and an image display ID, and may be used in conjunction with other devices, including a mesh tube MT, an occlusion device OD, and an introducer (not shown in FIG. 1), and with compositions such as a photochemical agent PA.

Catheter 110 may have an elongate catheter body 120 with a proximal end and a distal end suitable for insertion into a body lumen or cavity BL, such as a blood vessel, adjacent to a treatment region TR of the body lumen or cavity BL. Catheter body 120 may define an internal working channel 124, in which other components of catheter 110 can be disposed, and may be moveable therethrough. Thus, in some embodiments catheter body 120 may be inserted into the body of the patient, such as by delivery over a guidewire through the vasculature of the patient, until the distal end is disposed adjacent to the treatment region TR. The guidewire can then be removed and the other components of catheter 110 can be delivered through working channel 124 until their distal ends are disposed at the treatment region TR in appropriate working relation to the distal end of catheter body 120. In other embodiments, some or all of the other components of catheter 110 may be disposed in and/or coupled to catheter body 120 before catheter 110 is inserted into the body of the patient and the distal end delivered to the treatment region TR.

Catheter 110 includes a light emitter 130, which is disposed at the distal end of catheter body 120 when catheter 110 is configured for use. Light emitter 130 may be optically coupled to the light source LS by a light conduit 132, which may be disposed within catheter body 120, e.g. in working channel 124, and extends from the proximal to the distal end of the catheter body 120.

Catheter 110 also includes a fluid conduit 140, which may be disposed within catheter body 120 and extending from an inlet 144 at the proximal end of catheter body 120 to an outlet 142 at the distal end of catheter body 120. Fluid conduit 140 may be coupled at inlet 144 to the fluid source FS.

Catheter 110 may also include a spacing member 150 disposed at the distal end of catheter body 120. Depending on the implementation of spacing member 150, it may be attached to the distal end of catheter body 120 and actuated by fluid through fluid conduit 140. In some embodiments, spacing member 150 is coupled to or integrally formed with another component of the catheter 110. For example, the spacing member 150 can be formed with or coupled to inner body 148 (as described for example, with respect to FIG. 3D) that can now function as a spacing member actuator 152 that is disposed within catheter body 120. The spacing member actuator 152 extends from the proximal end to the distal end of the catheter body 120, and can be used to move the spacing member 150 between a collapsed configuration and an expanded configuration.

Catheter 110 may also include an imager 160 coupled to the distal end of catheter body 120. Imager 160 may be optically coupled to the image display ID by an imaging conduit 162 that may be disposed within catheter body 120 and extend from the proximal end to the distal end of catheter body 120.

Each component of treatment system 100 can be implemented in various ways. For applications in which catheter 110 is to be used to access treatment region TR of body lumen BL endovascularly, catheter 110 can be implemented as a conventional endovascular catheter, including its construction and materials, the ability to steer or not steer or deflect the distal end, to be deliverable over a guide wire or not, and include user controls and fittings at the proximal end. In some embodiments, the guide wire (not shown) can be disposed in working channel 124 of catheter body 120. In other embodiments, e.g., in which catheter body 120 may be relatively large, catheter body 120 may include a dedicated guide wire lumen, separate from working channel 124. The proximal portion of the catheter body 120 can be stiffer than the distal portion to provide sufficient rigidity for a user to push catheter body 120 over the guide wire and through the lumen, e.g., vasculature. The more flexible distal portion can facilitate navigation of catheter body 120 through, for example, tortuous vasculature. Catheter body 120 may be introduced into the body lumen BL, such as a blood vessel, via a cut down or other percutaneous technique for accessing the vessel lumen. In some applications, catheter 110 may be used to access treatment region TR directly, rather than through the subject's vasculature, and may be implemented accordingly. For example, if catheter 110 is used to access a treatment region TR directly through soft tissue, it may be implemented as a relatively rigid needle inserted through a trocar.

Light emitter 130 may be implemented with any known, suitable construction for emitting light of the desired wavelength and intensity from the distal end of catheter 110 to the treatment region TR of the body lumen BL. In some embodiments, light emitter 130 may simply be the end of an optical fiber, and the optical fiber may function as light conduit 132 to convey light from the light source LS coupleable to the proximal end of catheter 110. Light source LS may be any suitable source of light of the desired wavelength and intensity, and may be a source of coherent light such as a laser (pulsed or continuous wave), or incoherent light (such as a xenon or halogen light and a suitable bandpass filter). In other embodiments, light emitter 130 may be a relatively compact light source, e.g., a light emitting diode (LED) or a laser diode, disposed at the distal end of catheter 110, to which electrical power is provided by a conductor extending from the proximal end of catheter 110 through catheter body 120 to the light source. In alternative embodiments, a LED or a laser diode can be disposed at the proximal end of catheter 110.

Figure 2A:
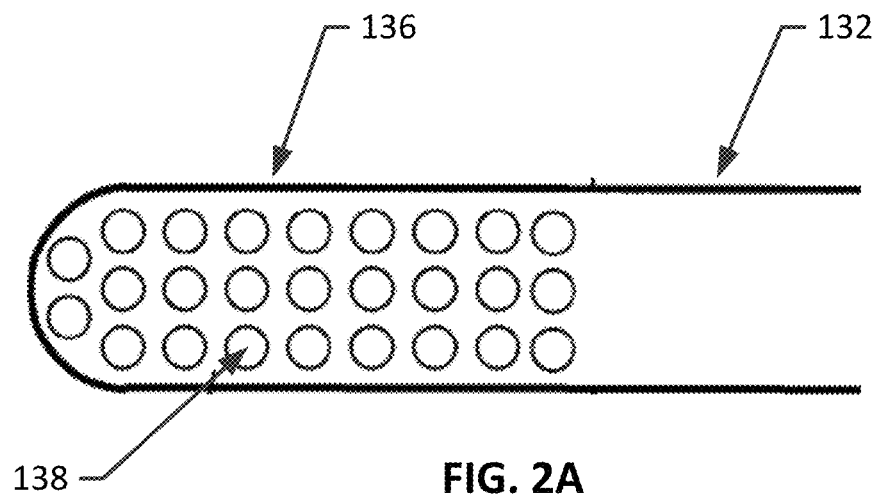
FIGS. 2A-2C are schematic illustrations of a light scatterer of the system of FIG. 1.

To produce a desired distribution of light at the treatment region TR, i.e., a distribution different from that produced by light source LS, in some embodiments a light scatterer 136 (see, e.g., FIG. 2A) is operatively associated with light source LS to scatter light from the light source LS across treatment region TR. In some embodiments, for example, as shown schematically in FIG. 2A, light scatterer 136 may be implemented as a convex end cap on the distal tip of light conduit 132, e.g., an optical fiber. The end cap may include light scattering particles, illustrated in FIG. 2A as circular regions 138. Such particles may be, for example, titanium dioxide. Other light scattering materials (high refractive index of ~2.5) or refracting structures may be used, such as, for example, diffraction gratings.

Figure 2B:
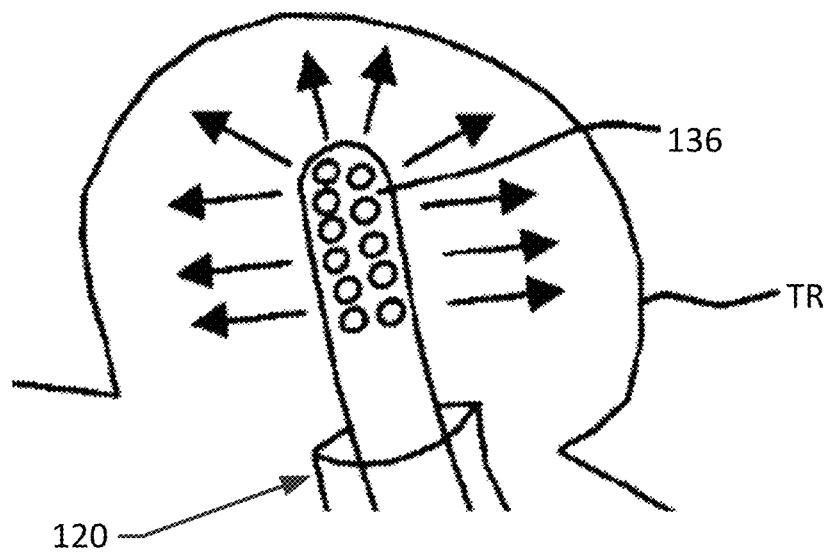
Figure 2C:
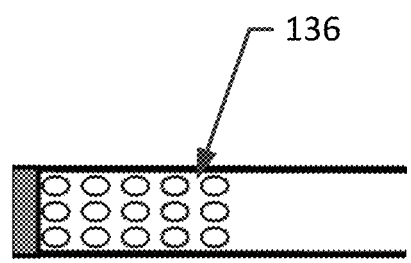

As shown schematically in FIG. 2B, the light emitter 130 is extended out a distal end of the catheter body 120, and the end cap and light scattering particles diffuse and distribute the light emitted from the distal tip of optical fiber 132 around the lateral sides of the tip and end cap to apply light to the treatment region TR, which in this instance is the surface of an aneurysm. The distribution pattern for the light may be tailored to the shape of the treatment region TR, with the objective of producing a relatively uniform energy density at the surface of treatment region TR, avoiding regions of excessively high energy density, i.e., "hot spots." For example, in the embodiment shown in FIG. 2B, the distribution is approximately spherical, to correlate with the approximately spherical shape of the vascular aneurysm that is the treatment region TR. In other embodiments, such as that shown in FIG. 2C, rather than a convex end cap, light scatterer 136 may be implemented as a cylindrical tip that scatters light only radially and not axially, thus producing a light distribution that better correlates to a cylindrical treatment region TR, such as the wall of a body lumen such as a blood vessel.

In other embodiments, described in more detail below with reference to FIG. 4E, the light scatterer 136 may be spaced from the light emitter 130, and instead be coupled to or form a portion of another structure, such as spacing member 150.

Fluid conduit 140 may be implemented with any known, suitable construction for conveying a fluid, such as saline, through catheter 110 to be discharged at the distal end of catheter body 120. The fluid may provide dilution, visualization, and/or cooling. For example, as shown schematically in FIGS. 3A and 3B, fluid conduit 140 may be an annular conduit defined between catheter body 120 and an inner body 148. Inner body 148 may provide a lumen or passage within which other structures, for example light conduit 132, may pass through catheter body 120. In the embodiment shown in FIGS. 3A and 3B, inner body 148 is a braided reinforcement or overwrap for optical fiber 132, to protect the delicate optical fiber and to provide a stiffer combined structure so that optical fiber, and attached scattering element 136, can be delivered distally through catheter body 120. Inner body 148 also supports light scatterer 136 on its distal end. In this embodiment, fluid conduit 140 is essentially the annular space left within the working channel 124 of catheter body 120 around inner body 148. In other embodiments, fluid conduit 140 may be arranged side-by-side with, rather than concentrically around, other structures such as light conduit 132. As shown schematically in FIG. 3A, outlet 142 may be configured simply as an opening at the annular distal end of the fluid conduit 140. In other embodiments, other geometries or structures may be employed to, for example, direct the flow of the dilution fluid laterally to the axis of catheter body 120, constrict the flow to reduce flow rate, accelerate the flow velocity, etc.

Figure 3B:
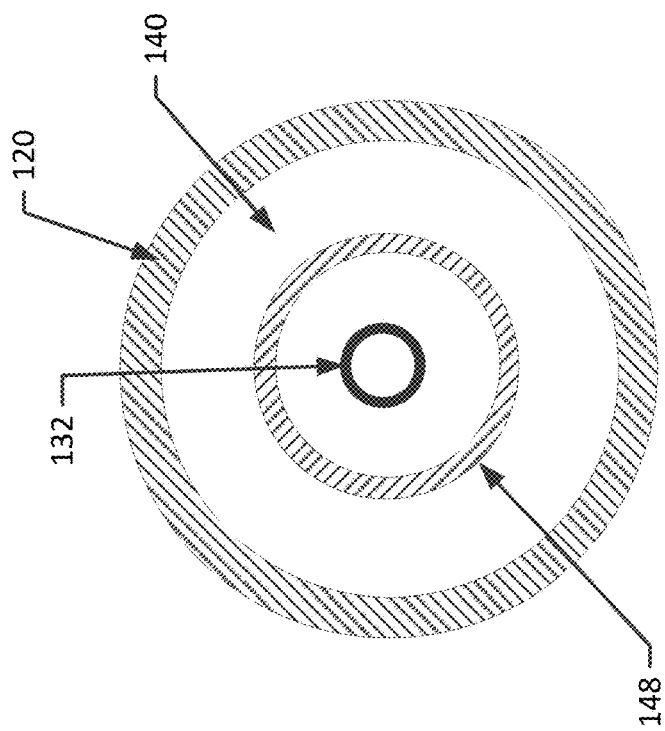
FIGS. 3A-3D are schematic illustrations of a fluid conduit and inner body for a light conduit of the system of FIG. 1.
Figure 3A:
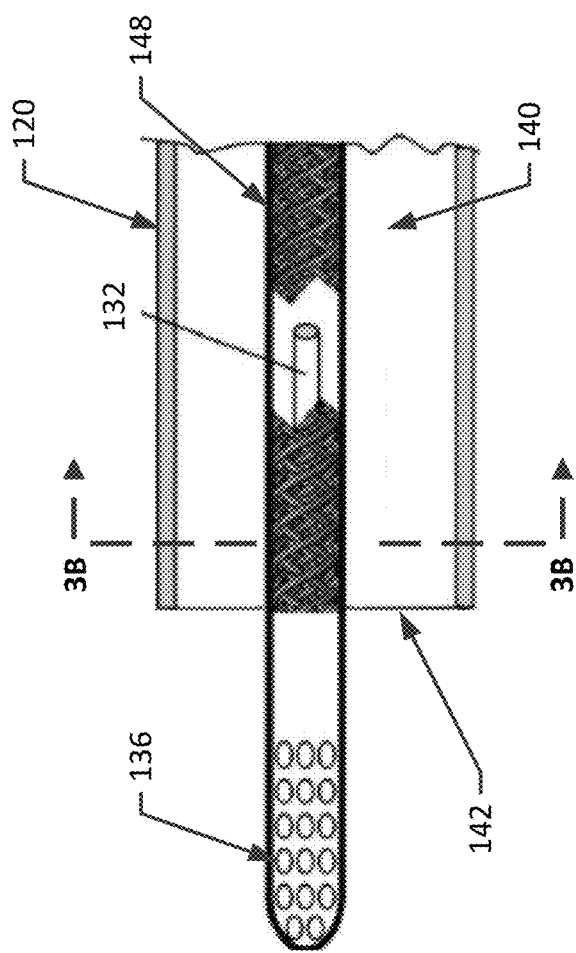
Figure 3C:
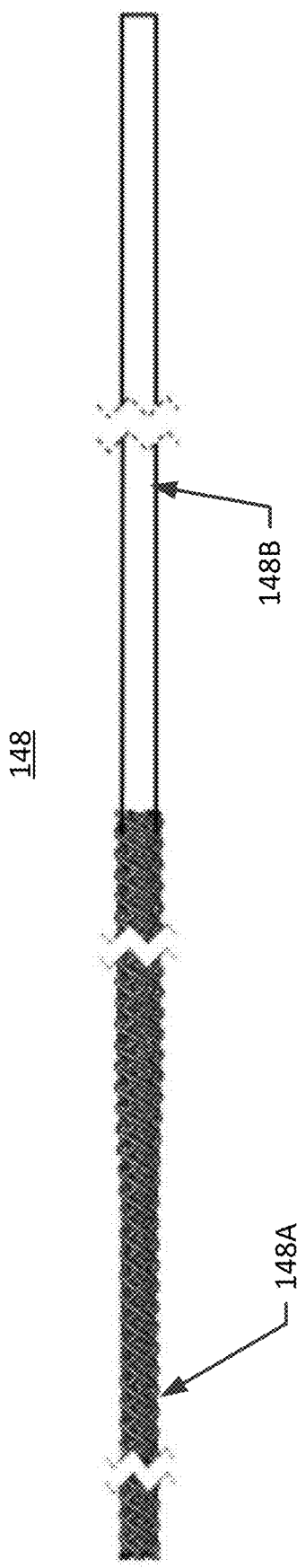
Figure 3D:
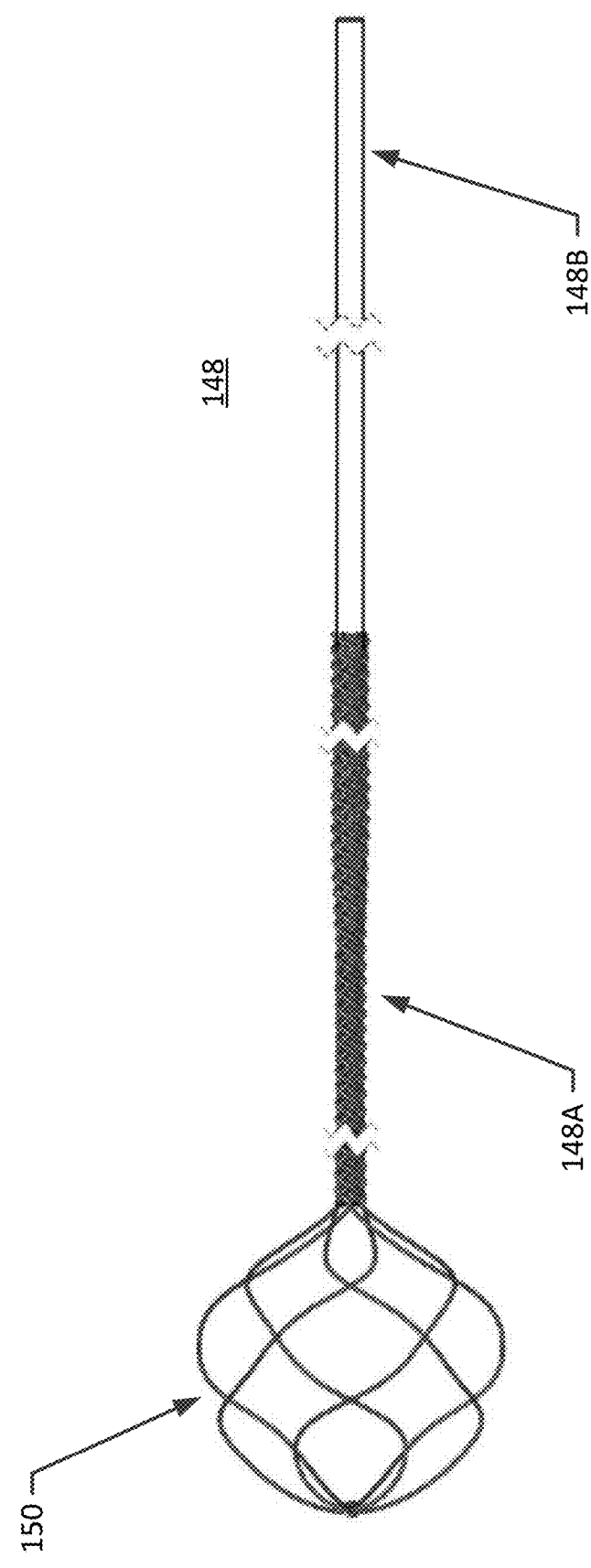

The inner body 148 of FIGS. 3A and 3B is shown in more detail in FIG. 3C. Inner body 148 has a distal portion 148A and a proximal portion 148B of different constructions. Proximal portion 148B may be formed as a solid tubular structure, e.g., a hypotube, that accounts for most of the length of inner body 148, e.g., 1 m, whereas the distal portion 148A may be formed as a braid or coil that accounts for a small portion of the length of inner body 148, e.g., about 25 cm. As described above, inner body 148 includes a central lumen that can receive the light conduit, such as optical fiber 132, and a distal tip on which the light scatterer 136 may be mounted. This construction provides a relatively stiff structure that enables the inner body 148 to be pushed distally through working channel 124 of catheter body 120, while the flexible distal portion 148A can be readily navigated into and through a tortuous body lumen BL. This embodiment is suitable for use with a catheter in which the spacing member 150 is coupled to the catheter body 110, as shown in FIGS. 4D-4G, described below. In an alternative embodiment, shown in FIG. 3D, spacing member 150 may be integrally formed with, or otherwise attached to the distal end 148A of inner body 148, as described in more detail below with reference to FIG. 4C.

Spacing member 150 may be implemented with a variety of structures and materials to provide the desired functions. A primary function of spacing member 150 is to maintain a minimum spacing between light emitter 130 and the treatment region TR, i.e., to prevent light emitter 130 from being disposed too close to treatment region TR, such that the light energy density of light emitter 130 is not above an acceptable upper limit. It may be further desirable for spacing member 150 to maintain a relatively uniform spacing between light emitter 130 and treatment region TR, for example keeping light emitter 130 relatively centered within body lumen BL. These related functions can be achieved in different ways. For example, in some embodiments, the light emitter 130 and spacing member 150 can be fixed relative to each other, and both can be moved through working channel 124 of catheter body 120 to the desired working position, as shown in FIG. 4C. In other embodiments, such as shown in FIGS. 4D and 4E, spacing member 150 may be fixed relative to catheter body 120, and light emitter 130 is movable relative to both.

Figure 4A:
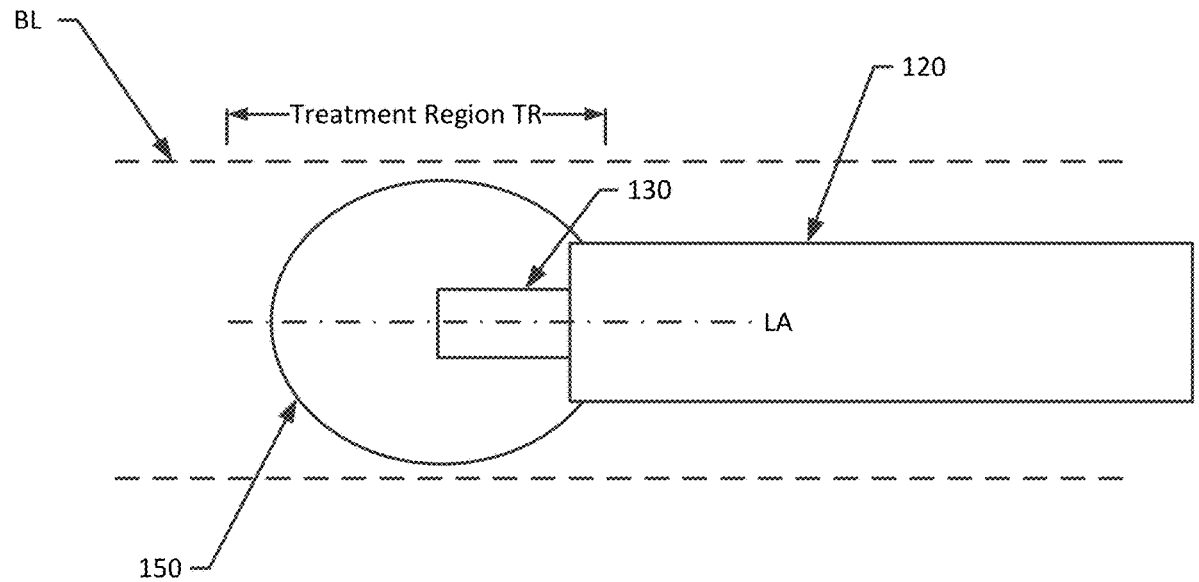
Figure 4B:
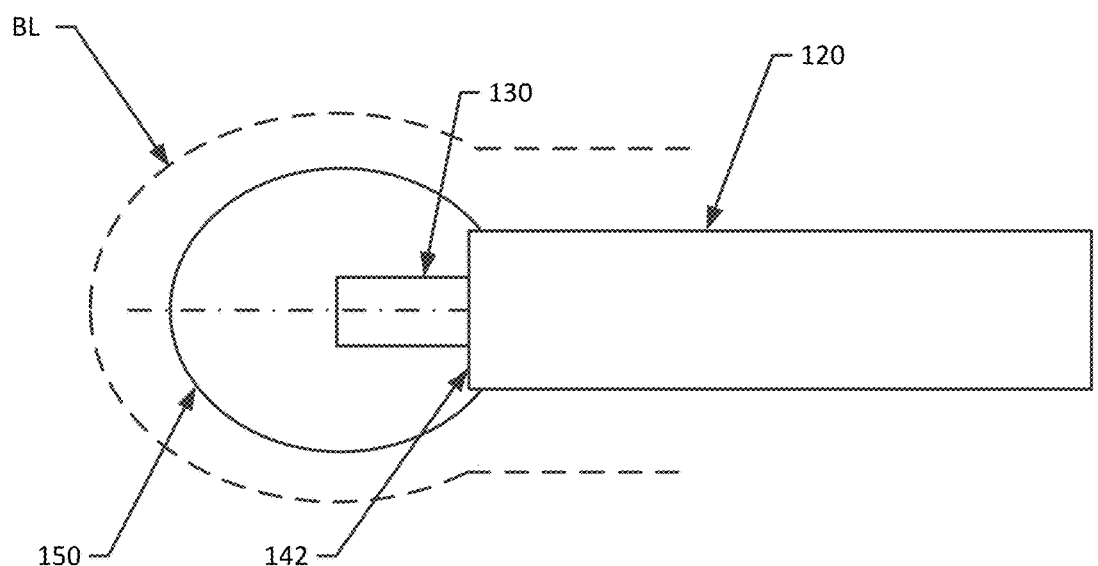

As shown schematically in FIG. 4A, with spacing member 150 having a shape or geometry that is approximately symmetrical about the longitudinal axis LA of catheter body 120, and with light emitter 130 disposed approximately on longitudinal axis LA, light emitter 130 is approximately centered within spacing member 150. When the catheter 110 is disposed within a body lumen BL, and spacing member 150 is in an expanded configuration in which its diameter is close to the diameter of body lumen BL, light emitter 130 is approximately centered in body lumen BL. If the light emitted by light emitter 130 is then relatively uniformly distributed angularly around longitudinal axis LA, the light energy density on treatment region TR will be relatively uniform circumferentially; said another way, the light energy density on treatment region TR will be between desired upper and lower energy density values. Although schematically illustrated in FIG. 4A as being ellipsoidal in shape, spacing member 150 may be configured to be of any other shape desired, depending for example on the shape of the body lumen and/or treatment region. As shown schematically in FIG. 4B, if the body lumen is a sac-like shape, for example, an aneurysm, rather than tube-like, for example, a blood vessel, an ellipsoidal or spherical shape may be more appropriate to best center light emitter 130 within body lumen BL.

Another function of spacing member 150 may be to permit dilution fluid DF to pass therethrough and into body lumen BL. For example, as described in more detail below, it may be desirable for spacing member 150 to be filled with the dilution fluid DF, e.g., to displace blood or other body fluid BF, and/or to cause or aid in reconfiguration of spacing member 150 from a collapsed to an expanded configuration. It may also be desirable for the dilution fluid to dilute and/or displace blood or other body fluid between spacing member 150 and the treatment region TR and/or body lumen BL. It may also be desirable to use the fluid to distend or otherwise change the geometry or shape of the treatment region TR and/or the body lumen BL. Thus, the side wall of spacing member 150 may be porous or otherwise permeable to the dilution fluid. In some embodiments, the proximal end of spacing member 150 may surround all or part of the outlet 142 of fluid conduit 140, as shown schematically in FIG. 4B, in which case the dilution fluid will enter the interior of spacing member 150 and the fluid can be passed out of spacing member 150 (e.g., through porous or permeable walls of spacing member 150). In other embodiments, outlet 142 of fluid conduit 140 may be disposed outside of spacing member 150, and it may be desirable to permit the fluid to enter spacing member 150.

Another function of the spacing member 150 may be to distend or otherwise change the geometry or shape of the treatment region TR and/or the body lumen BL mechanically, i.e., by engaging the spacing member 150 with the surface of treatment region TR and/or body lumen BL.

Several possible constructions of spacing member 150 are shown schematically in FIGS. 4C to 4E. In the embodiment shown in FIG. 4C, spacing member 150 can be in the form of a wire cage that is formed of multiple wires or struts 155, defining numerous apertures 157 therebetween, through which dilution fluid discharged by fluid outlet 142 may pass. Spacing member 150 may be formed of a braided wire, or a laser cut tube, or of other known constructions. Spacing member 150 may be self-expanding, for example may be formed of a shape memory material such as Nitinol, set or biased to the expanded configuration but retained in the collapsed configuration, for example by being disposed within the fluid conduit 140 (or working channel 124) of catheter body 120. Alternatively, spacing member 150 may be biased to the collapsed configuration and require application of a force to urge it towards the expanded configuration.

In the embodiment shown in FIG. 4D, spacing member 150 is formed of an elastomeric material, and thus is essentially a balloon. However, rather than being a sealed balloon it includes perforations 157 to permit passage of dilution fluid, and thus is referred to as a "leaky" balloon. The proximal end of spacing member 150 is disposed around fluid outlet 142, and thus dilution fluid discharged from fluid outlet 142 enters the interior of spacing member 150 and may exit via perforations 157. The dilution fluid may be used to flush the interior of the balloon, and expel any air via a bleed channel or tube (not shown) before the light emitter is 136 is inserted through working channel 124 of catheter body 120 (not shown) distally into position within spacing member 150. Dilution fluid may also be used to inflate the balloon, i.e. to urge spacing member 150 from a collapsed configuration (not shown) to the expanded configuration shown in FIG. 4D. As the balloon expands, the perforations 157 expand, and thus provide a larger flow area for the dilution fluid to exit the balloon. Thus, the size of the balloon may be controlled by controlling the flow rate and pressure of the dilution fluid exiting fluid outlet 142. After the treatment procedure, dilution fluid may be withdrawn from the elastic balloon, allowing the spacing member 150 to move to a collapsed configuration in which it can be withdrawn from the patient's body.

In the embodiment shown in FIG. 4E, spacing member 150 is also formed of an elastomeric material, and thus is also essentially a balloon. However, in this embodiment, the balloon is sealed, i.e., it does not include perforations as with the previous embodiment. Fluid may be introduced into body lumen BL via a port through catheter body 120 (not shown). As with the previous embodiment, the interior of the balloon may be flushed, purged of air, and then may be expanded, i.e., the spacing member 150 may be urged from a collapsed configuration (not shown) to the expanded configuration shown in FIG. 4E, by introduction of dilution fluid from fluid outlet 142. Thus, the size of the balloon may be controlled by controlling the amount of dilution fluid that exits fluid outlet 142. In this embodiment, spacing member 150 also provides some or all of the function of light scattering, in that it includes on an inner surface or an outer surface of the spacing member 150, a layer 135 (shown in the inner surface in FIG. 4E) of light scattering material. Although FIG. 4E schematically also illustrates a light scatterer 136 on the tip of light conduit 132, in some embodiments, the layer of material 135 on spacing member 150 may be the only light scatterer. In some embodiments, light scattering can be provided by light scattering particles mixed or suspended in the dilution fluid. In some embodiments, the spacing member 150 can be at least partially transmissive and/or transflective of the light emitted from the light emitter 130.

Figure 4G:
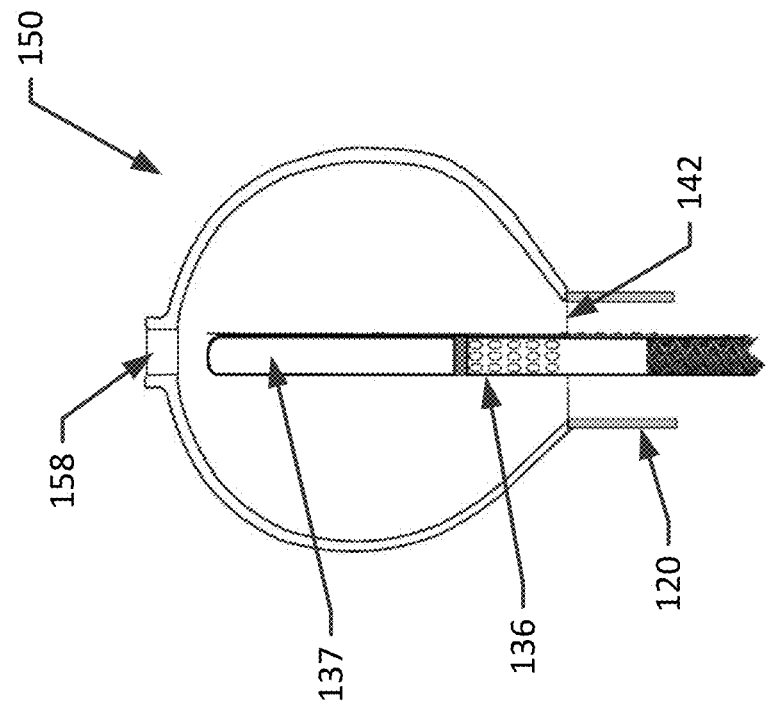
Figure 4F:
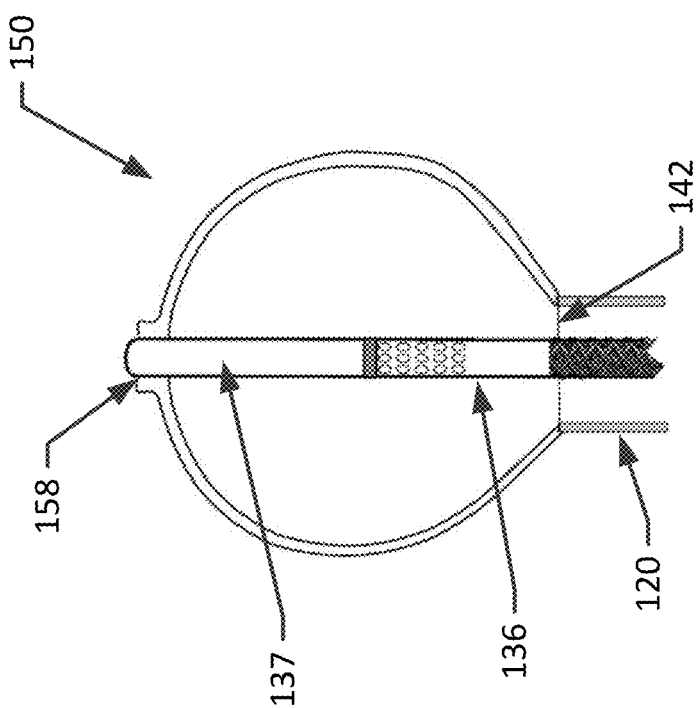

The embodiment shown in FIGS. 4F and 4G is similar to that shown in FIG. 4E, except that spacing member 150 includes a fluid port 158 in the distal end thereof, and light scatterer 136 includes a valve extension 137 on its distal tip. Valve extension 137 can cooperate with fluid port 158 to selectively establish and prevent fluid communication between body lumen BL and the interior of spacing member 150. For example, the valve extension functions as a closure element and the fluid port 158 of spacing member 150 provides a distal closure surface such that when the valve extension 137 is moved distally, a tight seal is formed between the surface of port 158 and the surface of valve extension 137. Thus, as shown in FIG. 4F, with valve extension 137 disposed in fluid port 158 to fluidically isolate the interior of elastic spacing member 150, fluid discharged from fluid outlet 142 can expand spacing member 150 to the desired configuration. Valve extension 137 can then be withdrawn proximally, and thus disengaged from fluid port 158, as shown in FIG. 4G, to establish fluidic communication between the interior of spacing member 150 and body lumen BL. Fluid discharged from fluid outlet 142 can then be discharged via fluid port 158 into body lumen BL.

Figure 5B:
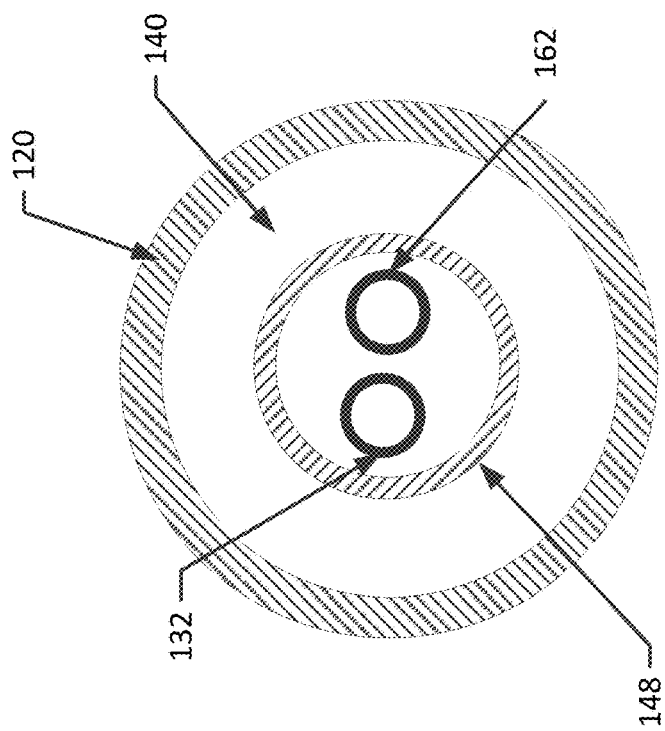
FIGS. 5A-5B are schematic illustrations of an imager of the system of FIG. 1.
Figure 5A:
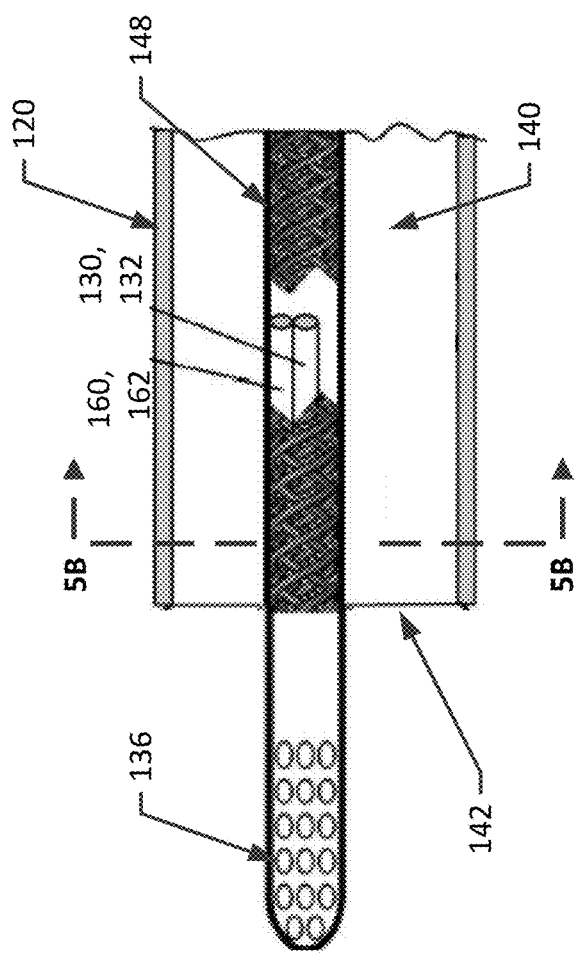

Imager 160 may be implemented with any known, suitable construction for collecting an image of treatment region TR or other portions of body lumen BL. Various imaging modalities may be employed, including optical (in wavelengths including visible, near infrared, and/or other portions of the spectrum), ultrasound, and optical coherence tomography (OCT). As shown schematically in FIGS. 5A and 5B, an imager 160 that is an optical imager in this example, may include an imaging conduit 162, for example an optical fiber. Imager 160 may provide a measurement of the light energy density applied to the treatment region TR by light emitter 130 over time, and thus the total energy applied. In other embodiments, imager 160 may enable acquisition of image information from treatment region TR, for example to aid in positioning of the distal end of the treatment system 100 relative to the treatment region TR, to evaluate the condition of the treatment region TR before, during, and after treatment, etc.

The light to be applied to treatment region TR, i.e., from light emitter 130, and optionally via light scatterer 136, may have wavelength(s) in the range of 400 nm to 1,000 nm. A convenient, and suitable, wavelength is 532 nm, which can be produced by readily available and inexpensive lasers and laser diodes. The power of the light applied to treatment region TR may be in the range from 1 mW to 500 mW, and preferably in a range of 100 mW to 200 mW. The power density of the light applied to treatment region TR may be in the range of 1 mW/cm$^2$ to 5 W/cm$^2$, preferably in a range of 50-500 mW/cm$^2$, and more preferably in a range of 175-200 mW/cm$^2$.

Although the mechanism of action is not well understood, it is believed that the application of light in the wavelengths and intensities described above may activate and/or accelerate hematopoiesis whereby stem cells differentiate to blood and blood vessel cells, which may then participate in rapid conversion of fresh thrombus to scar tissue and healing of the treatment region TR.

Mesh tube MT may be used in conjunction with catheter 110 in treatment of some indications and anatomical structures. Mesh tube MT may be of varied constructions, geometries, sizes, etc. suitable for the desired treatment. Examples of suitable mesh tubes are described in U.S. Pat. No. 7,942,925 to Yodfat et al., entitled "Implantable Intraluminal Device and Method of Using Same in Treating Aneurysms," the entire disclosure of which is incorporated by reference herein. One suitable embodiment of mesh tube MT is shown schematically in FIG. 6, in an expanded configuration in which mesh tube MT would be disposed within a body lumen BL. Mesh tube MT includes a plurality of filaments of elastic Or non-elastic bio-compatible material, metal or plastic, extending helically in an interlaced manner to define a braided tube. Thus, a first group of filaments MT1 extend helically in one direction, and a second group of filaments MT2 extend helically in the opposite direction, with the two groups of filaments being interwoven such that a filament MT1 overlies a filament MT2 at some points as shown at P1, and underlies a filament MT2 at other points as shown at P2. Filaments MT1 and MT2 thus define a braided tube having a plurality of windows W. The inscribed diameter and the length of each window W are shown at $W_d$ and $W_L$, respectively, in the implanted condition (e.g., expanded configuration) of the mesh tube MT. These characteristics depend on, among other factors: the number of filaments; the cross section of the filaments; and the implanted angle "α" at the cross-over points of the two groups of filaments MT1, MT2. Mesh tube MT may be disposed across the neck of a vascular aneurysm, along a straight section of a blood vessel or at or near a bifurcation of a blood vessel, and function to divert a portion of the blood flow through the vessel away from the aneurysm. The mesh tube MT can also be used to reduce blood flow to the selected part of a blood vessel in which blood coagulation is to be promoted. In some embodiments, the mesh tube MT is detached from the catheter 110 and deployed within the blood vessel. In some cases, the blood passing through the mesh tube MT into an aneurysm is subjected to a long residence time in the aneurysm, and therefore, platelets that have been activated during the passage into the aneurysm can initiate a thrombus formation that is now "jailed" or trapped inside the aneurysm. The light activation of the stem cells significantly accelerates the thrombus conversion to scar tissue and healing of the pathology.

Figure 7A:
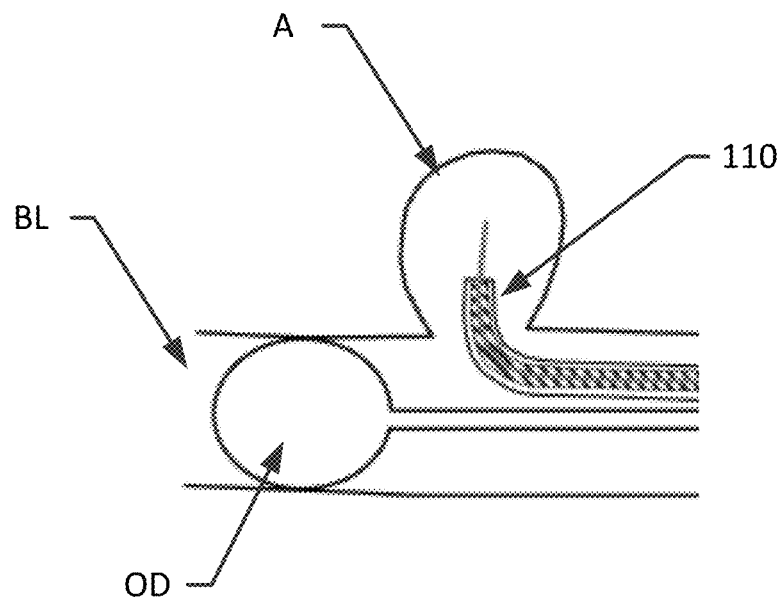
FIGS. 7A and 7B are schematic illustrations of occlusion devices usable with the system of FIG. 1.
Figure 7B:
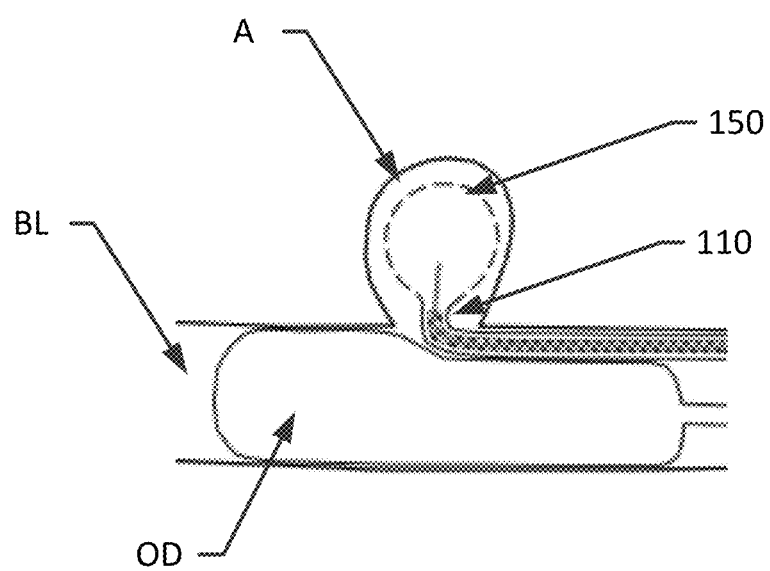

FIGS. 7A and 7B illustrate the use of an occlusion device OD that may be used in conjunction with catheter 110 in treatment of some indications and anatomical structures. As shown schematically in FIG. 7A, occlusion device OD may be placed in a body lumen BL, such as a blood vessel, and moved to an expanded configuration in which it engages the inner wall of body lumen BL and occludes it, i.e., reduces or prevents the flow of fluid, e.g. blood, through body lumen BL. In this embodiment, catheter 110 is shown with a distal end portion disposed in an aneurysm A upstream of occlusion device OD. As such, the catheter 110 can discharge fluid into aneurysm A and dilute blood therein to a desired dilution ratio without the fluid being carried away with blood through body lumen BL, since body lumen BL is occluded by occlusion device OD. In the embodiment in FIG. 7A, the distal tip of catheter 110 is steerable, and thus the light emitter may be disposed in a desired location within aneurysm A without the need for a spacing device. For delivery to the desired location in body lumen BL before treatment of the aneurysm A, and for withdrawal after conclusion of the treatment, occlusion device OD may be disposed in a collapsed configuration, and may be expanded to its expanded configuration to occlude body lumen BL by inflating the balloon with fluid, as is well known in the art. Suitable balloon occlusion devices include, for example, the HyperForm Occlusion Balloon distributed by Medtronic.

In another embodiment, shown in FIG. 7B, occlusion device OD may be an elongate balloon, such that it spans the neck of aneurysm A, and "jails" the distal tip of catheter 110. That is, the proximal portion of occlusion device OD can trap a portion of the distal end of catheter 110 against the wall of body lumen BL, thus immobilizing the catheter 110, in addition to occluding the lumen as with the previous embodiment. Suitable elongate balloon occlusion devices include, for example, the HyperGlide Occlusion Balloon distributed by Medtronic.

Figure 8:
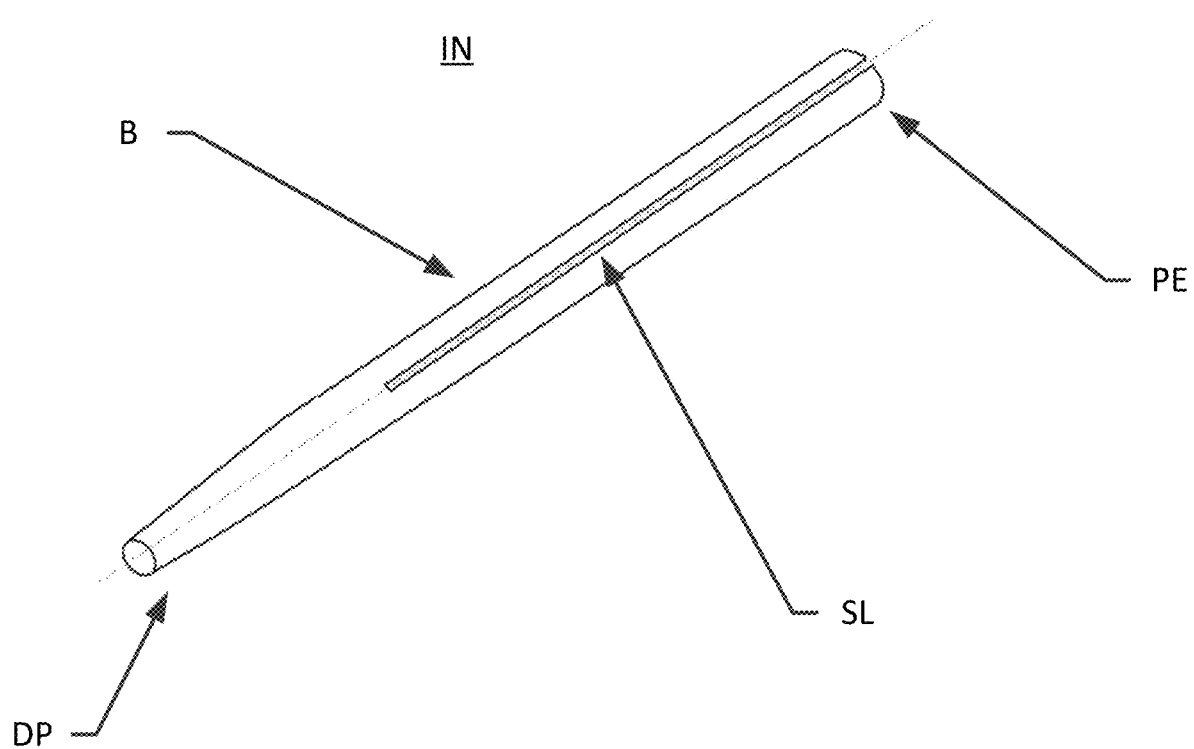
FIG. 8 is a schematic illustration of an introducer usable with the system of FIG. 1.
Figure 9:
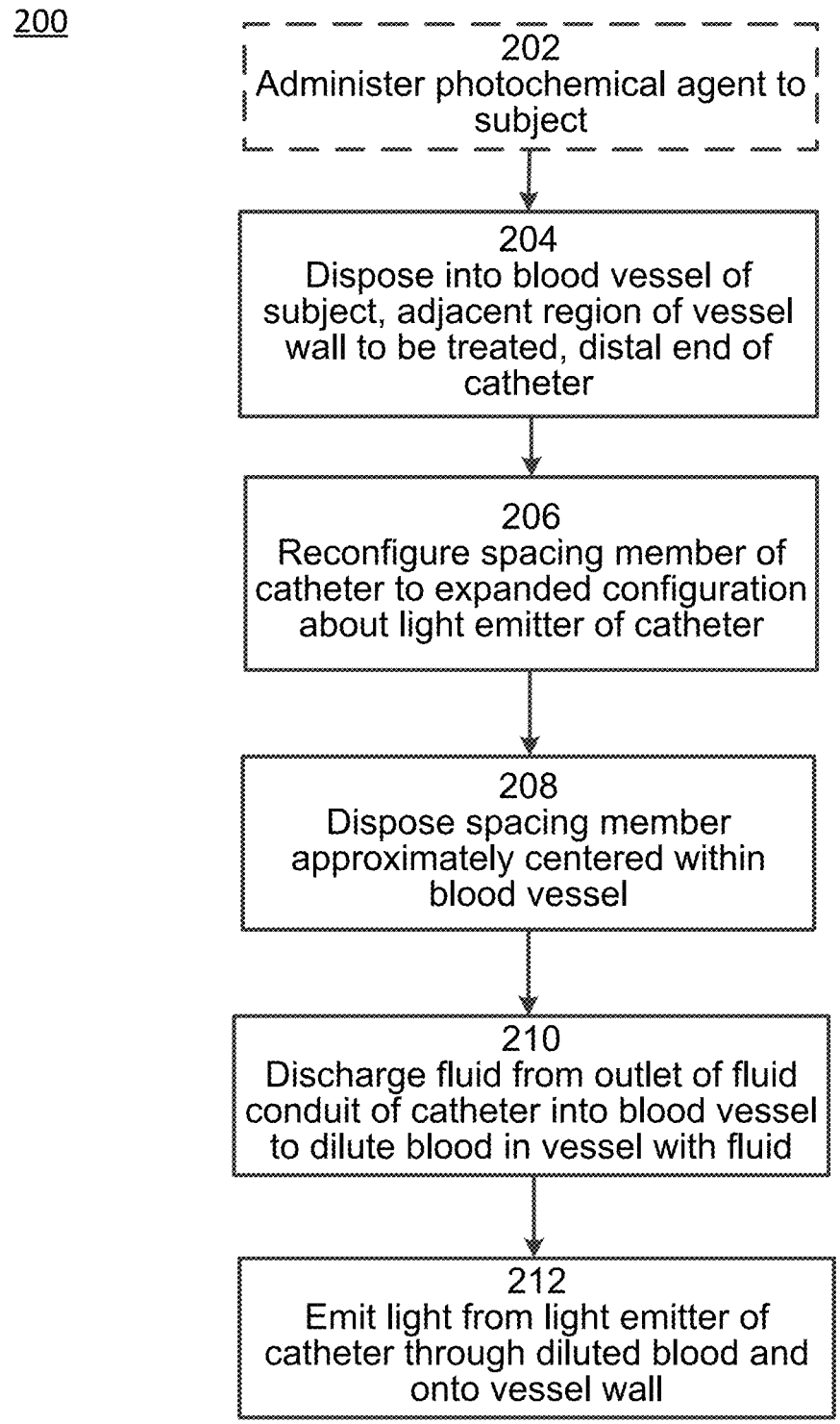
FIG. 9 a flowchart illustrating a method, according to an embodiment.

FIG. 8 illustrates an embodiment of an introducer IN that may be used in conjunction with catheter 110 in treatment of some indications and anatomical structures. Introducer IN has a generally cylindrical body B with a tapered distal portion DP, a proximal end PE, a central lumen extending through body B, and a slot SL in communication with the central lumen. The introducer IN can facilitate introduction of the inner body 148 into the catheter 110. For example, an incision or cutdown can be made in the patient's skin at the site where catheter 110 is to be introduced into the patient's body. Catheter 110 is then inserted into the patient's body through a standard introducer sheath. The proximal tip of catheter 110 is then fitted with a standard hemostatic valve. The tip of tapered distal portion DP can be inserted into the hemostatic valve, and introducer IN can be pushed into the hemostatic valve. When the distal end of introducer IN is in the desired position, the distal end of the inner body 148 can be inserted into the lumen of the introducer IN at proximal end PE and pushed through the lumen and out of the distal tip of introducer IN into the desired portion of the patient's anatomy, e.g., body lumen BL. Alternatively, the distal end of the inner body 148 can be preloaded into the lumen of the introducer IN A method of treating a treatment region TR of a body lumen, in particular a portion of a lumen wall of a blood vessel, is illustrated schematically in FIG. 9. At 202, an optional photochemical agent can be administered to the subject (e.g., patient) to be treated. For example, a light-energy absorption agent, or a biochemical thrombosing agent, may also be applied to the interior of the selected part of the blood vessel to be treated, including the neck and all layers of the malformation. In some cases, a photochemical agent such as erythrosin B or rose bengal can be infused into the treatment region of the blood vessel before irradiation to enhance light absorption by the vascular wall and accelerate the photochemical reaction. The agent can be administered intravenously (IV) (i.e., systemically) or locally into blood vessel (or aneurysm or malformation) to be treated either through catheter 110 or via a separate microcatheter. Thereafter, an optical translucent or transparent field is established before the light energy is applied thereto.

At 204, a catheter (e.g., catheter 110) can be inserted into a blood vessel of the subject and a distal end of the catheter can be disposed adjacent or near a region of a vessel wall to be treated. In some embodiments, prior to inserting the catheter into the blood vessel, a guide wire is inserted into the blood vessel and positioned near the treatment region. The catheter can then be inserted over the guide wire (e.g., a lumen of the catheter can be received over the guidewire) and moved along the guidewire to the desired location at the treatment region.

At 206, a spacing member (e.g., spacing member 150) and a light emitter 130 (e.g., light emitter 130 with light scatterer 136) of the catheter 110 can be moved out a distal end of a lumen of the catheter 110, and the spacing member can be moved to an expanded configuration about the light emitter. The spacing member can prevent contact between the light emitter and the blood vessel wall and can ensure the centering of the light emitter within the blood vessel such that an even distribution of the photon energy flux to the surrounding vessel walls can be achieved. At 208, the spacing member can be positioned approximately centered within the blood vessel to be treated.

At 210, fluid can be discharged from an outlet of the fluid conduit of the catheter 110, and into the blood vessel to dilute blood within the blood vessel. For example, infusion of saline can be started to establish a clear or translucent optical field within the treatment region of the blood vessel. At 212, light energy can be emitted from the light emitter of catheter through the diluted blood and onto the wall of the blood vessel. The light energy can initiate and/or accelerate coagulation of blood therein within the treatment region, during which, the spacing member can prevent emboli, resulting from the coagulation, from moving through the blood vessel in the downstream direction. In some cases, the spacing member can be detached from the delivery system and remain permanently in the therapeutic site for protection. After treatment, the catheter can be removed from the blood vessel.

Figure 10:
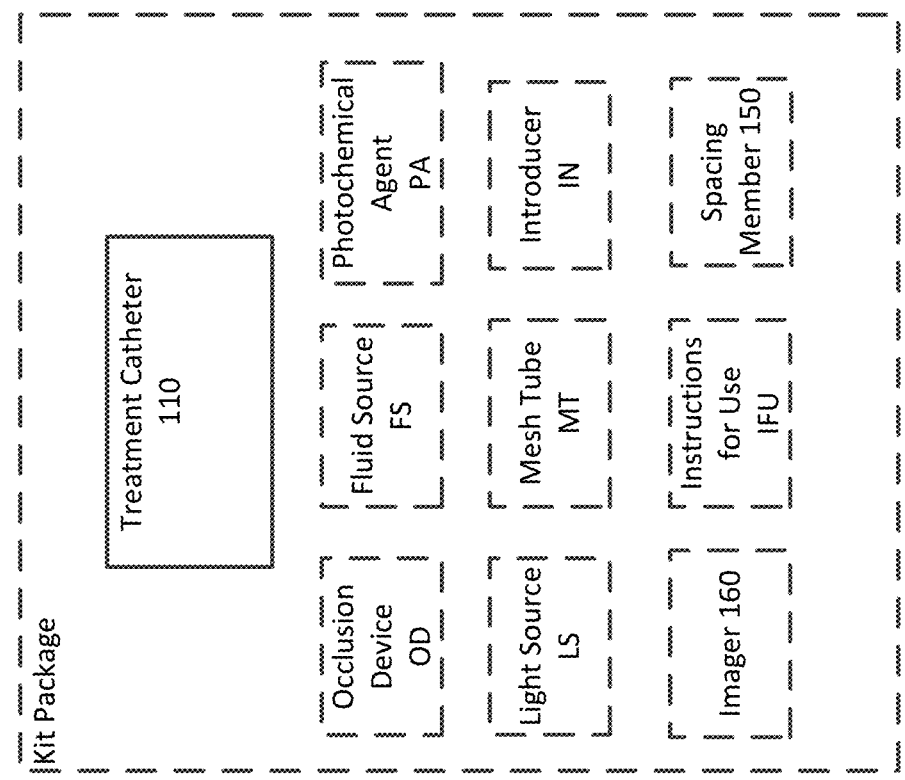
FIG. 10 is a schematic illustration of a kit including elements of a system for use in a method according to an embodiment.

FIG. 10. is a schematic illustration of a kit, according to an embodiment. As described above, a treatment system 100 can be provided as a kit that includes one or more components to perform various functions to treat a treatment region TR. In some embodiments, a KIT can be a single use set of disposable components. In some embodiments, a KIT can include a catheter 110 disposed within a kit package, such as a sterile package used to protect the catheter 110 from contamination during transport and storage. In some embodiments, a kit package can include an outer package and one or more inner sterile packaging components to contain and protect one or more of the components of the KIT. The catheter 110 can include, for example, a catheter body 120 with a working channel 124, a light emitter 130, and a fluid conduit 140, as described above. A KIT can also optionally include one or more of each of the following components that can be used in conjunction with the catheter 110: an occlusion device OD, a light source LS, a fluid source FS, a photochemical agent PA, a mesh tube MT, an introducer IN, a spacing member 150, an imager 160, and/or instructions for use IFU. In some embodiments, a KIT can include, for example, multiple types of spacing member (e.g., 150) such that a user (e.g., physician) can select the appropriate spacing member 150 for a particular treatment. In some embodiments, a KIT can include, for example, multiple types of light emitter (e.g., 130) such that a user (e.g., physician) can select the appropriate light emitter 130 (e.g., with various types of a light scatterer 136, etc.), for a particular treatment. Each of the components of a KIT can be disposed within one or more sterile kit packages.

FIGS. 11A-11E illustrate various approaches to using treatment systems such as those described above to treat an aneurysm disposed laterally off a side wall of a blood vessel. The embodiments and particular components of the treatment systems shown and described with respect to FIGS. 11A-11E can be constructed the same as or similar to, and include the same or similar features as corresponding components of the system 100 described above. The system and components shown can be used to treat the aneurysm with, for example, light energy, as described above.

In the treatment approach shown in FIG. 11A, the treatment system includes a catheter 210 with a distal end portion of the catheter 210 disposed within an aneurysm A disposed laterally off a side wall of a blood vessel BV. The catheter 210 may include any of the features described above, the details of which are omitted from FIG. 11A for simplicity. For example, spacing member 250 disposed at the distal end of the catheter body 224 may be implemented with any of the options described above, include a porous balloon, a non-porous balloon, a wire cage, etc. The spacing member 250 can be moved between a collapsed configuration (not shown) during delivery to the treatment site and an expanded configuration (shown in FIG. 11A) during the treatment procedure using any of the techniques described above. The spacing member 250 can be used to maintain a minimum spacing between the light emitter 230 and the walls of the aneurysm A to be treated. With the light emitter 230 and spacing member 250 disposed within the aneurysm A, the light emitter 230 can be actuated to emit a desired light energy to treat the aneurysm. Optionally, a fluid (e.g., saline) can be introduced into the treatment region as described above.

In the approach illustrated in FIG. 11B, the catheter 210 is being used in conjunction with a mesh tube 246. The mesh tube 246 can be formed and configured the same as or similar to the mesh tube MT described with respect to FIG. 6. The mesh tube 246 can be disposed within the blood vessel BV outside the aneurysm A such that it extends across (i.e., straddles) the opening of the aneurysm A. The mesh tube 246 can be deployed in a contracted or collapsed configuration and moved to an expanded configuration within the blood vessel BV. In this embodiment, the catheter 210 is inserted between the wall of the blood vessel BV and the mesh tube 246 prior to the mesh tube 246 being expanded. The mesh tube 246 is then expanded such that the mesh tube 246 holds or traps the catheter 210 against the wall of the blood vessel BV during treatment with the light emitter 230. A fluid (e.g., saline) can be introduced into the treatment region to establish a clear or translucent optical field and light energy is then applied via the light emitter 230 to irradiate the therapeutic target vessel wall to initiate or accelerate coagulation of the blood within the aneurysm. The mesh tube 246 can prevent emboli resulting from the coagulation from moving into the blood vessel. The mesh tube 246 can also function to divert a portion of the blood flow through the blood vessel BY away from the aneurysm A.

Figure 6:
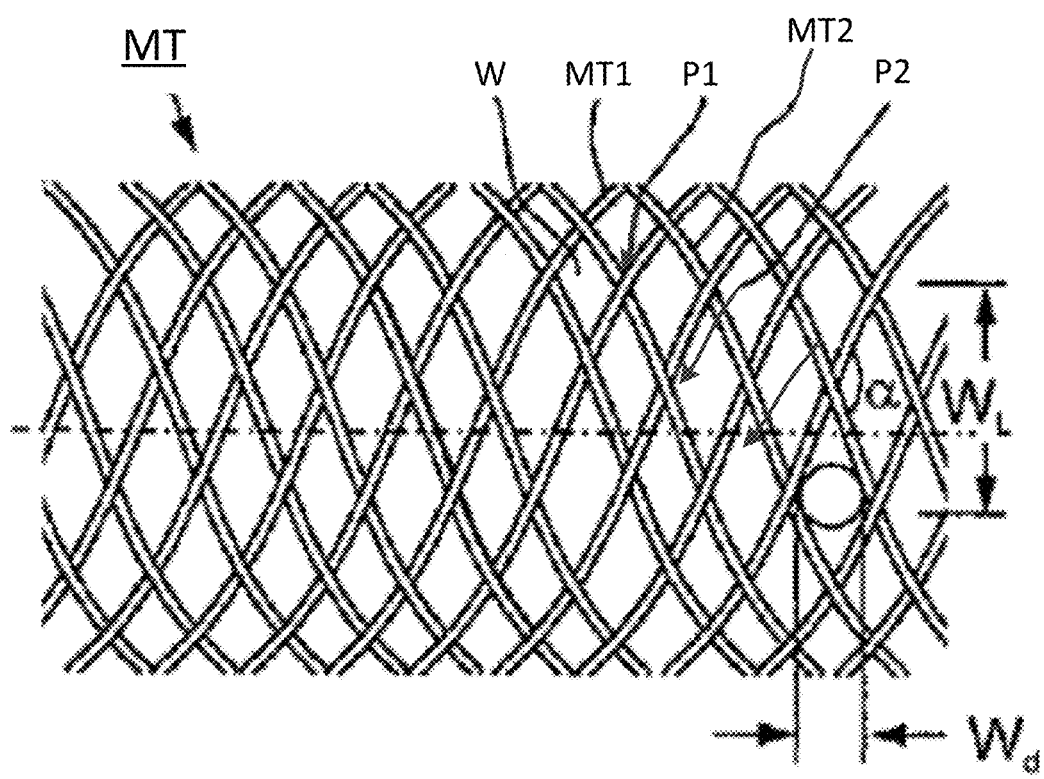
FIG. 6 is a schematic illustration of a mesh tube usable with the system of FIG. 1.

The approach illustrated in FIG. 11C is similar to that illustrated in FIG. 11B except that the catheter 210 is being used in conjunction with a mesh tube 246', which can be formed and configured the same as or similar to the mesh tube MT described with respect to FIG. 6. The mesh tube 246' can be disposed within the blood vessel BV outside the aneurysm A such that it extends across (i.e., straddles) the opening of the aneurysm A. In this approach, the mesh tube 246' is expanded at the treatment location before the catheter 210 is inserted through a lumen defined by the mesh tube 246' and inserted out a side wall of the mesh tube 246' and into the aneurysm. The mesh tube 246' can function to divert a portion of the blood flow through the blood vessel BY away from the aneurysm A. The mesh tube 246' can also help maintain the position of the catheter 210 in relation to the aneurysm A during treatment with the light emitter 230. Fluid can be injected into the treatment region and light energy applied via the light emitter 230 as described above.

In the approach illustrated in FIG. 11D, catheter 210 is being used in conjunction with an occlusion device 254. The occlusion device 254 can be formed and configured the same as or similar to the occlusion device OD described above with respect to FIGS. 7A and 7B. For example, the occlusion device 254 can be an expandable balloon that can be moved between a collapsed configuration for delivery to the treatment location within the blood vessel BV, and an expanded configuration as shown in FIG. 11D. The occlusion device 254 can be disposed within the blood vessel BV in the collapsed configuration and deployed into the blood vessel outside the aneurysm A such that it extends across (i.e., straddles) the opening of the aneurysm A. The catheter 210 is inserted between the wall of the blood vessel BV and the occlusion device 254, and then the occlusion device 254 is moved to its expanded configuration such that the occlusion device 254 holds or traps the catheter 210 against the wall of the blood vessel BV. Fluid (e.g., saline) can be introduced into the treatment region to establish a clear or translucent optical field, and light energy is then applied via the light emitter 230 to irradiate the therapeutic target vessel wall to initiate or accelerate coagulation of the blood within the aneurysm A. During the light treatment, the occlusion device 254 prevents emboli resulting from the coagulation from moving into the blood vessel BV. The occlusion device 254 can also obstruct the flow of blood within the blood vessel during treatment of the aneurysm A. In the approach illustrated in FIG. 11E, a catheter 210' has a steerable distal end portion, and thus can be used without the spacing member 250. A distal end portion of the catheter 210' is disposed within an aneurysm A as described for FIG. 11A with the light emitter 230 approximately centered within the aneurysm A by the steering control for the distal end portion. In this illustration, the catheter 210' is being used in conjunction with an occlusion device 254'. The occlusion device 254' can be formed and configured the same as or similar to the occlusion device OD described above with respect to FIGS. 7A and 7B. For example, the occlusion device 254' can be an expandable balloon that can be moved between a collapsed configuration for delivery to the treatment location within the blood vessel BV to an expanded configuration as shown in FIG. 11E.

In this approach, the occlusion device 254' is deployed into the blood vessel BV in a collapsed configuration to a position downstream of the aneurysm A to block the flow of blood through the blood vessel BV, and then expanded to fix the occlusion device 254 within the blood vessel distal of the aneurysm A. The catheter 210' is inserted between an inflation conduit of the occlusion device 254' and the wall of the blood vessel BV, and the distal end portion steered so that light emitter 230 is approximately centered in the aneurysm A. Fluid (e.g., saline) can be introduced into the treatment region to establish a clear or translucent optical field, and light energy is then applied via the light emitter 230 to irradiate the therapeutic target vessel wall to initiate or accelerate coagulation of the blood within the aneurysm A. During the light treatment, the occlusion device 254 also prevents emboli resulting from the coagulation from moving downstream into the blood vessel BV.

FIGS. 12A-12E illustrate various approaches to using treatment systems such as those disclosed above to treat an aneurysm disposed at a bifurcation in a blood vessel. The embodiments and particular components of the treatment systems shown and described with respect to FIGS. 12A-12E can be constructed the same as or similar to and include the same or similar features as corresponding components of the system 100 described above. The system and components shown can be used to treat the aneurysm with, for example, light energy, as described above.

In the treatment approach shown in FIG. 12A, the treatment system includes a catheter 310 with a distal end portion of the catheter 310 disposed within an aneurysm A disposed at a bifurcation BF of a blood vessel BV. The catheter 310 may include any of the features described above, the details of which are omitted from FIG. 12A for simplicity.

For example, spacing member 350 disposed at the distal end of the catheter body 324 may be implemented with any of the options described above, including a porous balloon, a non-porous balloon, a wire cage, etc. The spacing member 350 can be moved between a collapsed configuration (not shown) for delivery to the treatment location and an expanded configuration (shown in FIG. 12A) during treatment using any of the techniques described above. The spacing member 350 can be used to maintain a minimum spacing between the light emitter 330 and the walls of the aneurysm A to be treated.

The catheter 310 is inserted into the blood vessel BV and the distal end portion of the catheter 310, including the spacing member 350 and light emitter 330, are disposed within the aneurysm A. The spacing member 350 is moved to its expanded configuration and fluid is injected to establish a clear or translucent optical field. Light energy is then applied via the light emitter 330 to initiate and/or accelerate coagulation of blood at the treatment region. The spacing member 350 can help prevent emboli, resulting from the coagulation, from moving into the blood vessels in the downstream direction.

In the approach illustrated in FIG. 12B, the catheter 310 is being used in conjunction with a mesh tube 346 and a mesh tube 347 to further secure emboli from migrating into the blood vessels during treatment. The mesh tubes 346 and 347 can also serve as scaffold for vascular remodeling after photon therapy as well as serving as a filter for preventing emboli from migrating into the blood vessel. The mesh tubes 346 and 347 can be formed and configured the same as or similar to the mesh tube MT described with respect to FIG. 6. The mesh tube 346 includes a first portion that can be disposed within the blood vessel BV outside the aneurysm A and a second portion that extends into a branch B1 of the blood vessel BV. Similarly, mesh tube 347 includes a first portion that can be disposed within the blood vessel BV outside the aneurysm A engaging the mesh tube 346 and a second portion that extends into a branch B2 of the blood vessel BV. The mesh tubes 346 and 347 can be delivered in a collapsed configuration and moved to an expanded configuration at the treatment location. In this embodiment, the mesh tube 346 and the mesh tube 347 collectively define an elongate space between each other within the blood vessel BV and that terminates at the opening of the aneurysm. The distal end portion of the catheter 310 can be inserted between the vessel wall and the elongate space defined by the mesh tubes 346 and 347, effectively being "jailed" between the vessel wall and the mesh tube. Spacing member 350 and light emitter 330 are inserted into the aneurysm A, and the spacing member 350 can then be expanded within the aneurysm A and fluid injected to establish a clear or translucent optical field. Light energy is then applied via the light emitter 330 to initiate and/or accelerate coagulation of blood at the treatment region. The mesh tube as well as the spacing member 350 can also help prevent emboli, resulting from the coagulation, from moving into the blood vessels in the downstream direction.

The approach illustrated in FIG. 12C is similar to that illustrated in FIG. 12B, except in this illustration, the catheter 310 is being used in conjunction with a mesh tube 346' and a mesh tube 347', which can be formed and configured the same as or similar to the mesh tube MT described with respect to FIG. 6. The mesh tube 346' includes a first portion that can be disposed within the blood vessel BV outside the aneurysm A and a second portion that can extend into a branch B1 of the blood vessel BV. Similarly, mesh tube 347' includes a first portion that can be disposed within the blood vessel BV outside the aneurysm A and a second portion that can extend into a branch B2 of the blood vessel BV. In this embodiment, the mesh tube 346' and the mesh tube 347' abut each other within the blood vessel BV such that collectively the mesh tubes 346' and 347' are substantially Y-shaped (called the "double barrel technique"). In this embodiment, the catheter 310 is inserted and the distal end portion positioned within the aneurysm A, prior to the mesh tubes 346' and 347' being inserted into the blood vessel BV. After the catheter 310 is positioned, the mesh tubes 346' and 347' can be positioned within the blood vessel BV and branches B1 and B2 and expanded such that the mesh tubes 346' and 347' hold or trap the catheter 310 in the space formed between the mesh tubes 346' and 347' and the artery wall. The mesh tubes 346' and 347' can function to divert a portion of the blood flow through the blood vessel BV away from the aneurysm A. The mesh tubes 346' and 347' can also help maintain the position of the catheter 310 relative to the aneurysm during treatment with the light emitter 330.

In the approach of FIG. 12D, the catheter 310 is being used in conjunction with a single mesh tube 346", which can be formed and configured the same as or similar to the mesh tube MT described with respect to FIG. 6. In this embodiment, the mesh tube 346" includes a first portion that extends into the branch B1 and second portion that extends into the branch B2 of the blood vessel BV. The catheter 310 is inserted into the aneurysm and mesh tube 346" is then opened to the expanded position essentially trapping the catheter 310 between the artery wall and the mesh tube 346" with its distal tip inside aneurysm A as shown in FIG. 12D. The mesh tube 346" can also help maintain the position of the catheter 310 relative to the aneurysm A during treatment with the light emitter 330.

In the approach illustrated in FIG. 12E, the catheter 310 is being used in conjunction with a single mesh tube 346''', which can be formed and configured the same as or similar to the mesh tube MT described with respect to FIG. 6. The mesh tube 346''' is substantially Y-shaped and includes a middle portion disposed within the blood vessel BV outside the opening of the aneurysm A, and two branch portions that extend into the branch B1 and branch B2 of the blood vessel BV. In this embodiment, the catheter 310 is inserted into the aneurysm A and then the mesh tube 346''' is moved to the open position essentially "jailing" or trapping catheter 310 between the artery wall and the mesh tube 346''' as shown in FIG. 12E. The mesh tube 346''' can also help maintain the position of the catheter 310 relative to the aneurysm during treatment with the light emitter 330.

Figure 13:
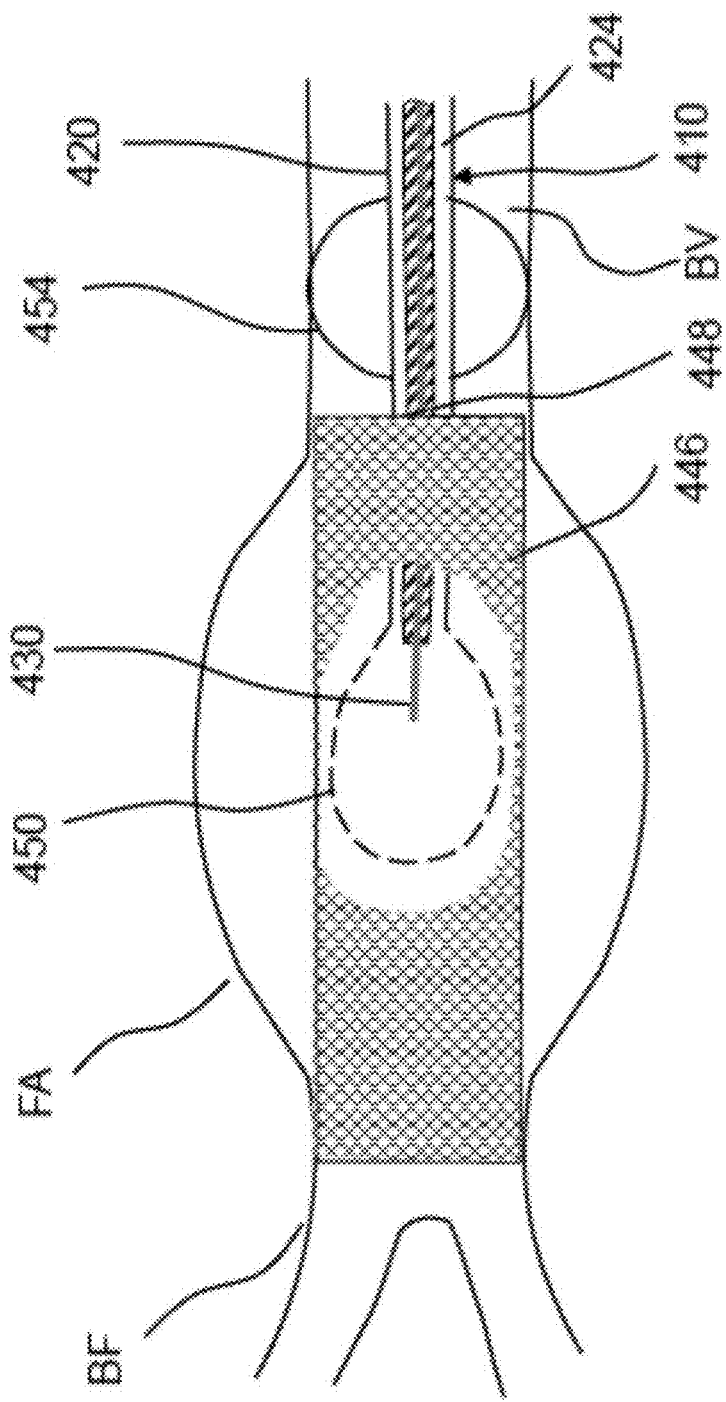
FIG. 13 is a schematic illustration of a device and method for treating a fusiform aneurysm in a blood vessel, according to an embodiment.

FIG. 13 illustrates the use of a treatment system, such as those described above, to treat a fusiform aneurysm FA disposed at a wall of a blood vessel BV near a bifurcation BF. The embodiments and particular components of the treatment system shown and described with respect to FIG. 13 can be constructed the same as or similar to and include the same or similar features as corresponding components of the system 100 described above. The system and components shown can be used to treat the fusiform aneurysm FA with, for example, light energy, as described above.

As shown in FIG. 13, the treatment system includes a catheter 410 shown with a distal end portion of the catheter 410 disposed within a fusiform aneurysm FA disposed at a side wall of a blood vessel BV. The catheter 410 may include any of the features described above, the details of which are omitted from FIG. 12A for simplicity.

The spacing member 450 may be implemented with any of the options described above, include a porous balloon, a non-porous balloon, a wire cage, etc. The spacing member 450 can be moved between a collapsed configuration (not shown) and an expanded configuration (shown in FIG. 13) using any of the techniques described above. The spacing member 450 can be used to maintain a minimum spacing between the light emitter 430 and the walls of the fusiform aneurysm FA to be treated. With the light emitter 430 and spacing member 450 disposed within the fusiform aneurysm FA, the light emitter 430 can be actuated to emit a desired light intensity to treat the aneurysm.

In this embodiment, the catheter 410 includes an occlusion device 454 coupled to the catheter body 420. The occlusion device 454 can be formed and configured the same as or similar to the occlusion device OD described above with respect to FIGS. 7A and 7B. For example, the occlusion device 454 can be an expandable balloon that can be moved between a collapsed configuration for delivery to the treatment location within the blood vessel BV and an expanded configuration as shown in FIG. 13. In this embodiment, the occlusion device 454 is disposed within the blood vessel BV ahead of the fusiform aneurysm FA to impede or to block the flow of blood through the blood vessel BV.

The catheter 410 can also be used in conjunction with a mesh tube 446, as shown for example in FIG. 13, which can be formed and configured the same as or similar to the mesh tube MT described with respect to FIG. 6. In this embodiment, the mesh tube 446 is elongate and is shown disposed inside the blood vessel BV traversing the fusiform aneurysm FA with "landing zones" in the artery on both ends of the aneurysm FA. The catheter 410 is inserted through a lumen defined by the mesh tube 446 and remains disposed within the lumen of the mesh tube 446 during treatment of the fusiform aneurysm FA with the light emitter 430.

Figure 14:
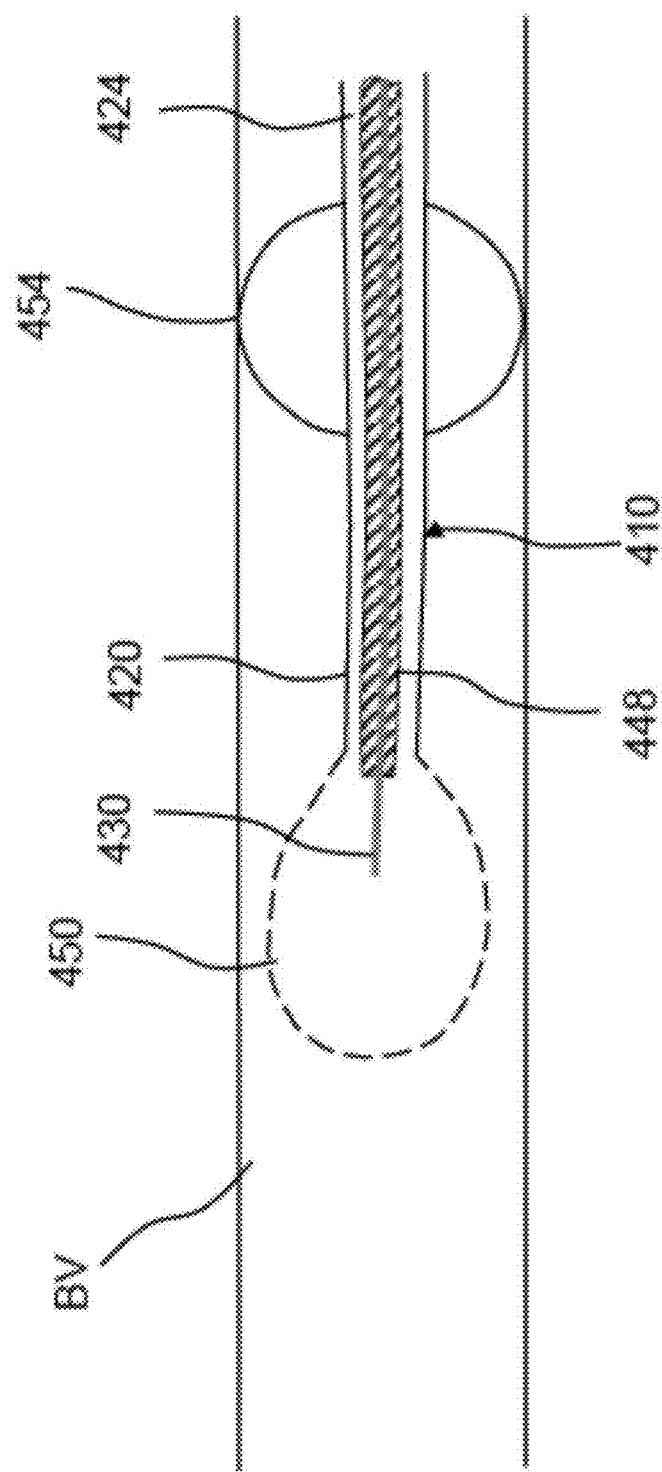
FIG. 14 is a schematic illustration of a device and method for occluding a blood vessel, according to an embodiment.

FIG. 14 illustrates the catheter 410 disposed within a blood vessel BV illustrating use of the catheter 410 for treatment of a wall of the blood vessel BV (for example, to treat a varicose vein) and using the occlusion device 454 to occlude blood flow within the blood vessel BV during treatment, for example, with the light emitter 430.

Figure 15:
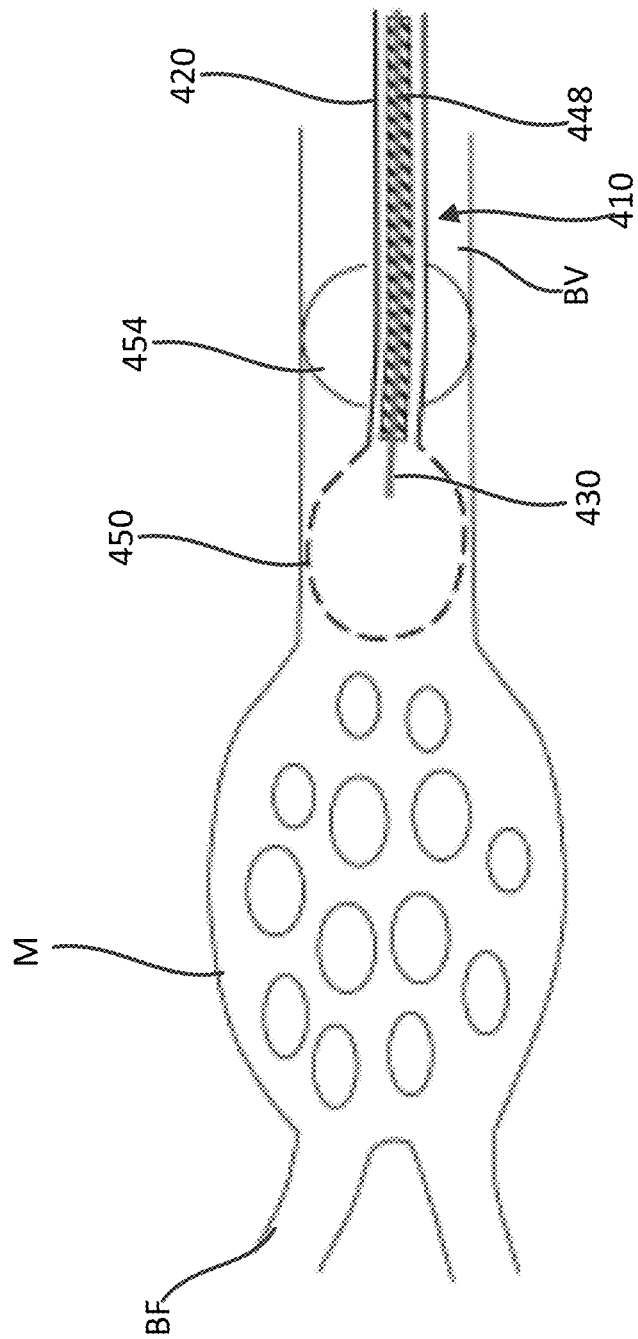
FIG. 15 is a schematic illustration of a device and method for embolizing a malformation in a blood vessel, according to an embodiment.

FIG. 15 illustrates the catheter 410 disposed within a blood vessel BV to treat a malformation M within the blood vessel BV. In FIG. 15, the bifurcation BF at the exit of the malformation M is illustrative of potentially multiple exits from the malformation M. In this example, the catheter 410 that includes an occlusion device 454 coupled to the catheter body 420 is positioned within the blood vessel BV leading directly into the malformation. Spacing member 450 is moved to the open position and fluid flow is initiated through flow channel 440. Irradiation of the malformation M is started by light emitted from the light emitter 430 to embolize the malformation within the blood vessel BV. Light penetration into the small frail arteries of the malformation M can initiate thrombus formation, followed by its conversion to scar tissue and can result in excluding the malformation M from the circulation.

Figure 16:
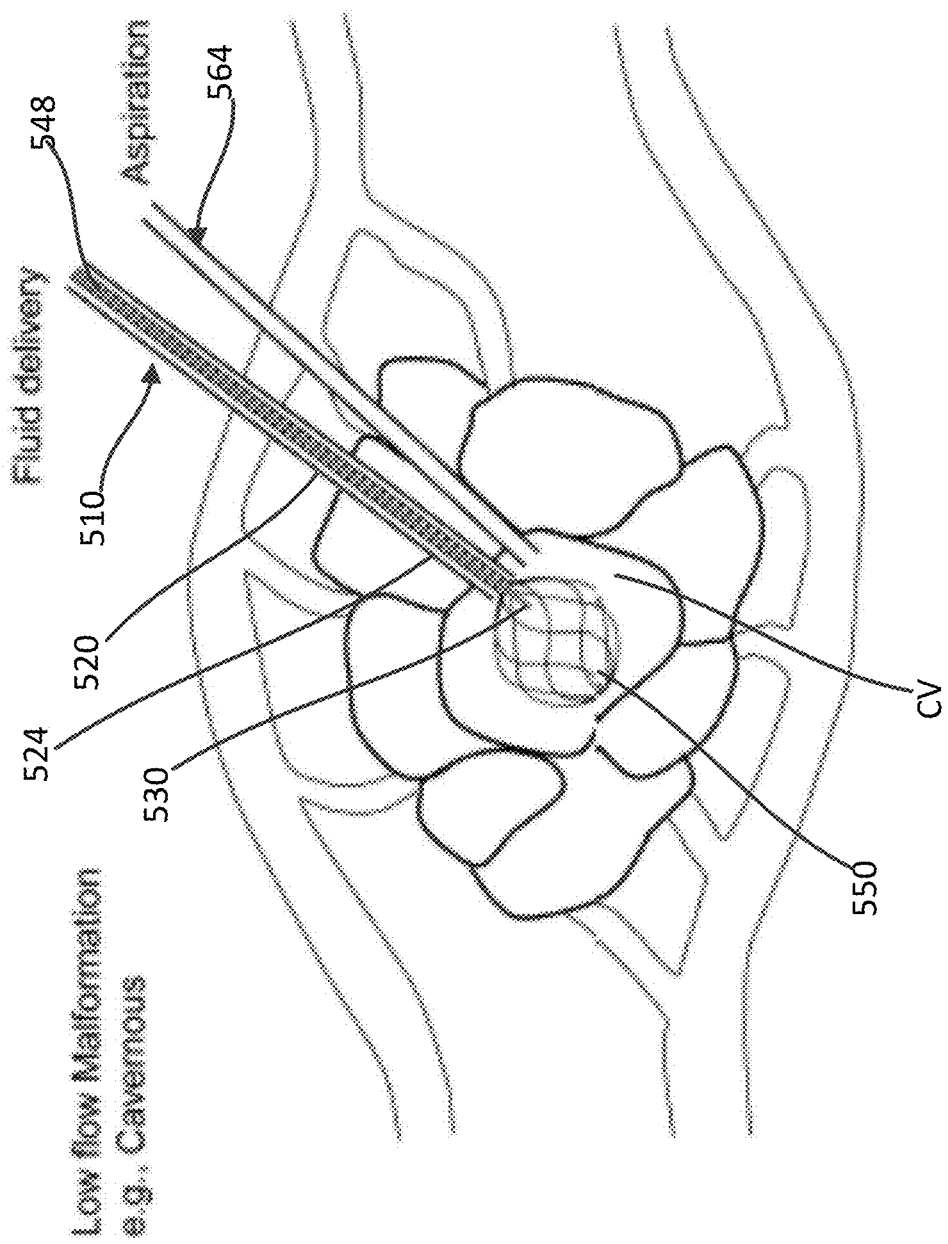
FIG. 16 is a schematic illustration of a device and method for treating a cavernous malformation, according to an embodiment.

FIG. 16 illustrates components of a treatment system, such as those described above, being used to treat a low flow malformation, for example, a cavernous malformation within a subject's body. The embodiments and particular components of the treatment system shown and described with respect to FIG. 16 can be constructed the same as or similar to and include the same or similar features as corresponding components of the system 100 described above. The system and components shown can be used to embolize a malformation with, for example, light energy, as described above.

As shown in FIG. 16, the treatment system includes a catheter 510 shown with a distal end portion of the catheter 510 disposed within a cavernous region CV. The catheter 510 may include any of the features described above, the details of which are omitted from FIG. 16 for simplicity. In some embodiments, catheter 510 can be a blunt needle inserted over a trocar into the lesion.

For example, spacing member 550 is disposed at the distal end of the catheter body 520 through working channel 524. The spacing member 550 shown in FIG. 16 is constructed the same or similar to the spacing member 150 shown and described with respect to FIG. 4C. More specifically, the spacing member 550 includes multiple wires or struts that define numerous apertures therebetween through which dilution fluid discharged by the catheter 410 may pass. The spacing member 550 can be used to maintain a minimum spacing between the light emitter 530 and the walls of the treatment region. Any of the other spacing member designs described above can be used.

In this treatment approach, the catheter 510 is inserted into the cavernous malformation directly through the skin and intervening tissue of the patient (e.g., percutaneously), rather than intra arterially or intravenously. For example, the catheter 510 can be introduced into the patient's body via a delivery sheath inserted into the body through an opening in the skin and/or bony structures such as the skull of the patient's body. In this embodiment, the working channel 524 of the catheter body 520 can be used to introduce or inject fluid from a fluid source (not shown) into the treatment region, i.e., the cavernous region CV. A separate aspiration device 564 can be used to aspirate (e.g., remove) excess fluid and/or other material from the treatment region. In some embodiments, the catheter 510 can include an aspiration channel incorporated with the catheter body 524. Examples of such an embodiment are described below with respect to FIGS. 17A-17H.

Figure 17A:
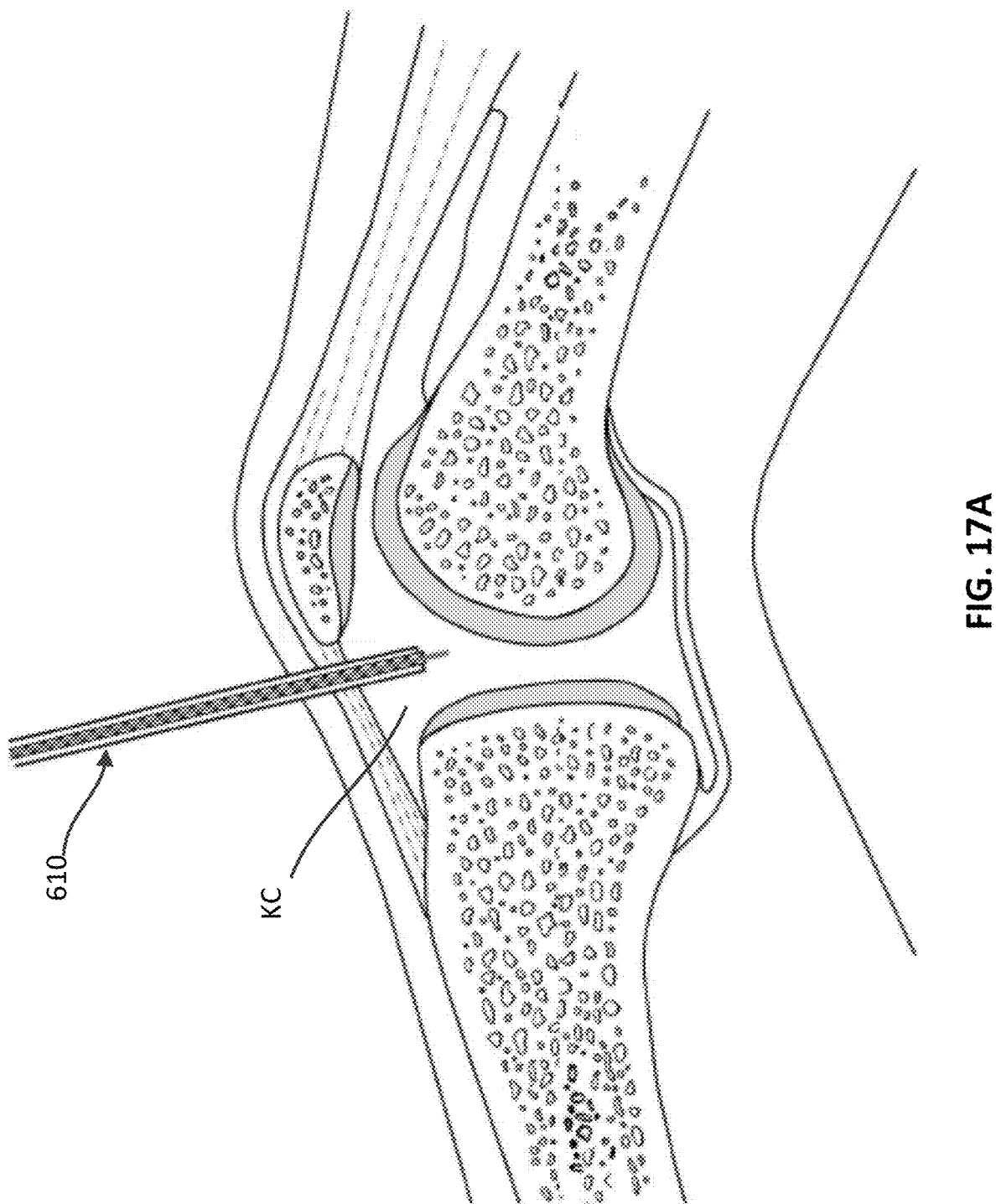
FIG. 17A is a schematic illustration of a device and method for treating a joint, e.g., a knee capsule.

FIGS. 17A-17C illustrate components of a treatment system being used to treat, for example, a cavernous malformation or a joint, e.g., a knee capsule KC (FIG. 17A). The embodiments and particular components of the treatment system shown and described with respect to FIGS. 17A-17C can be constructed the same as or similar to and include the same or similar features as corresponding components of the system 100 described above. The system and components shown can be used to treat the treatment region within the knee capsule KC with, for example, light energy, as described above.

As with the previous embodiment of FIG. 16, the treatment system is introduced directly (e.g., percutaneously) into the joint (e.g., knee capsule) of the patient, as shown in FIGS. 17A-17C. The treatment system includes a catheter 610 (e.g., a blunt needle) shown with a distal end portion of the catheter 610 disposed within a knee capsule KC. The catheter 610 includes a catheter body 620 that defines a lumen 624 through which an inner body 648 is movably disposed. The lumen 624 can also be used to introduce fluid (e.g., saline) from a fluid source (not shown) into the treatment region. In this embodiment, the inner body 648 defines a lumen 633 (see FIG. 17C) that can receive therein an optical fiber (not shown) coupled to a light emitter 630. Light scattering elements can be incorporated into light emitter 630 and attached to inner body 648. The light emitter 630 (and optical fiber) can be coupled to a light source (not shown). Since fluid in body joints is transparent or translucent, no dilution of such fluid with a transparent fluid such as saline is necessary in order to have the light irradiation reach the soft tissue to be treated. Further, if light scattering material that is fully transmissive, e.g., diamond dust, is used no cooling is required.

FIGS. 17D and 17E illustrate another embodiment of a catheter that can provide fluid flush and aspiration functions, and can be used, for example, to treat a joint, such as a knee capsule KC, as shown in FIG. 17A. The catheter 710 includes a catheter body 720 that defines a lumen 724 through which an inner body 748 is movably disposed. The inner body 748 defines a lumen 733 (see FIG. 17E) that can receive therein an optical fiber (not shown) coupled to a light emitter 730. Although not shown, light scattering elements can also be attached to or incorporated with light emitter 730. The light emitter 730 (and optical fiber) can be coupled to a light source (not shown).

In this embodiment, the lumen 724 of the catheter body 720 can also be used to introduce or convey a fluid, such as a saline, from a fluid source (not shown) into the treatment region, e.g., a cavernous malformation or a knee capsule KC. The fluid can exit the lumen 724 through a distal opening or outlet 742. As described previously, the fluid may provide dilution, visualization, and/or cooling within the treatment region. The catheter body 720 also defines a separate aspiration lumen 766 disposed parallel to the lumen 724. The aspiration lumen can be used to aspirate (e.g., remove) excess fluid from the treatment region, for example, either continuously during treatment or when the light treatment is completed.

Figure 17F:
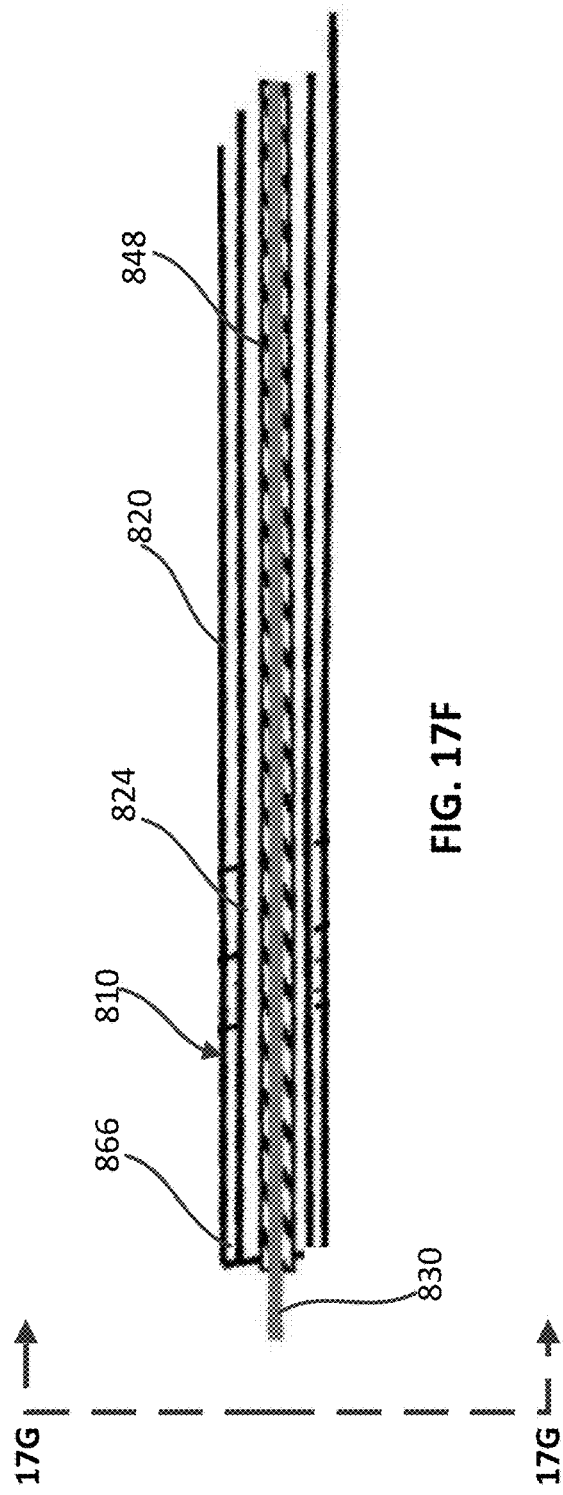
FIGS. 17F and 17G are side and end views, respectively, of yet another alternative embodiment of a device suitable for use in the method for treating a joint as shown in FIG. 17A.
Figure 17G:
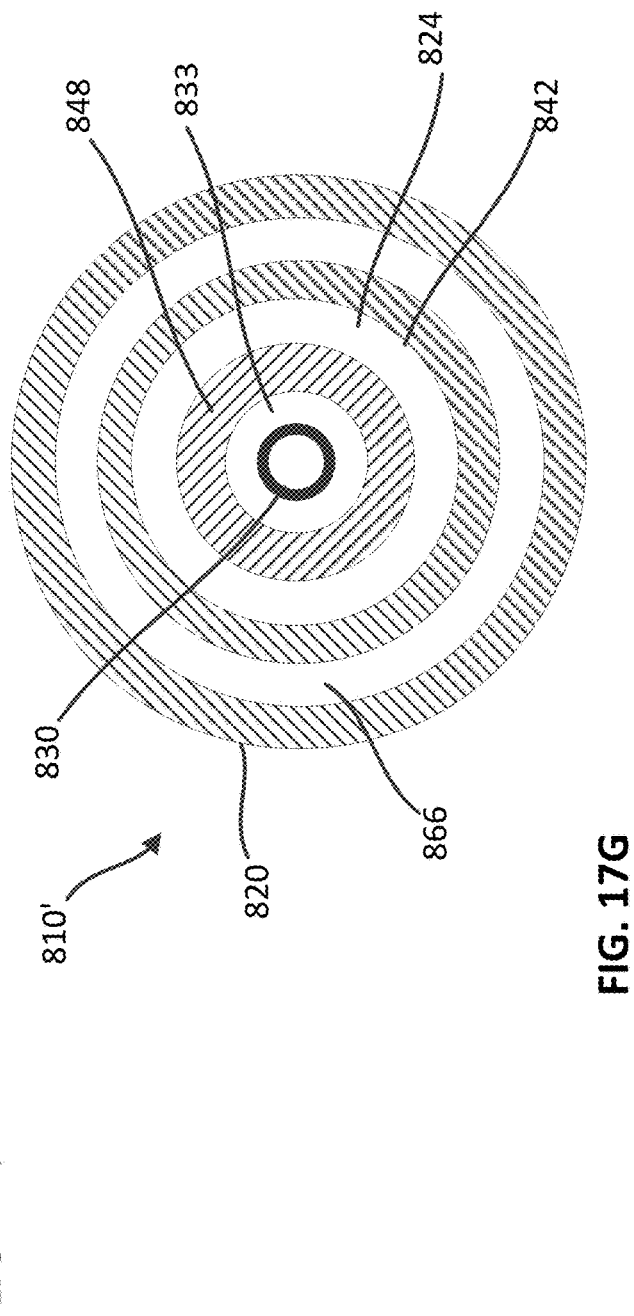

FIGS. 17F and 17G illustrate another alternative embodiment of a catheter that can provide fluid flush and aspiration functions, and can be used, for example, to treat a joint, such as a knee capsule KC or a cavernous malformation, as shown in FIG. 17A and FIG. 16, respectively. The catheter 810 includes a catheter body 820 that defines a lumen 824 through which an inner body 848 is movably disposed. The inner body 848 defines a lumen 833 (see FIG. 17G) that receives therein an optical fiber (not shown) coupled to a light emitter 830. Although not shown, a light scattering element can also be attached to or incorporated with light emitter 830. The light emitter 830 (and optical fiber) can be coupled to a light source (not shown).

In this embodiment, the lumen 824 of the catheter body 820 can also be used to introduce or convey a fluid from a fluid source (not shown) into the treatment region, e.g., a cavernous malformation or a knee capsule KC. The fluid can exit the lumen 824 through a distal opening or outlet 842. The catheter body 820 also defines an aspiration lumen 866 that can be used to aspirate the treatment region (e.g., remove fluid and/or other material from the treatment region). In this embodiment, the lumen 824 (used for introducing fluid) and the aspiration lumen 866 are coaxial. Alternatively, the lumen 824 could be used for aspiration and the lumen 866 could be used for conveying fluid into the treatment region.

Figure 17H:
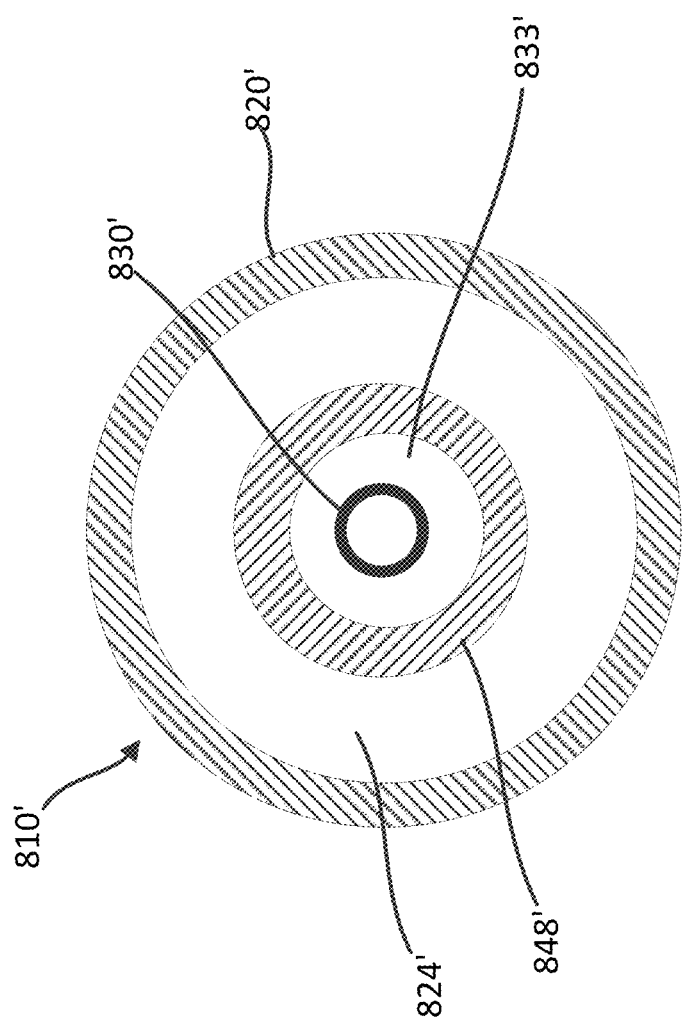
FIG. 17H is an end view of an alternative embodiment of a device suitable for use in the method for treating a joint as shown in FIG. 17A.

In an alternative embodiment shown in FIG. 17H, a catheter 810' can include a catheter body 820' that defines a lumen 824' that can be used to both convey a fluid into a treatment region and aspirate the treatment region. For example, the catheter body 824' can be coupled to a fluid source to convey fluid into the treatment region. The flow of fluid to the lumen 824' can then be terminated and the catheter body 820' can be coupled to a device to provide for aspiration through the lumen 824'. Alternately, lumen 824' can be coupled to a valve that switches between a fluid irrigation source and an aspiration source.

The invention claimed is:

1. An apparatus comprising:
a catheter having a catheter body with a distal end and a proximal end, the catheter defining a conduit;
an inner body configured to be movably disposed within the conduit;
a light emitter disposed on a distal tip of the inner body and configured to emit light; and
a spacing member configured to be disposed distal of the catheter body and transitioned from a collapsed configuration to an expanded configuration, in the expanded configuration the spacing member configured to (1) have a distal-most end disposable distally of the distal end of the catheter body and the light emitter, and (2) be disposed about the light emitter and to maintain the light emitter approximately centered relative to at least one axis of the spacing member,
the apparatus configured for the distal end of the catheter body to be inserted at least partially into a body lumen or cavity having an interior wall, for the spacing member to be transitioned to the expanded configuration within the body lumen or cavity, and for light to be emitted from the light emitter to illuminate the interior wall of the body lumen or cavity, a diameter of the spacing member in the expanded configuration being equal to or less than an inner dimension of the body lumen or cavity.

2. The apparatus of claim 1, wherein the conduit has an inlet couplable to a source of fluid and an outlet disposed at the distal end of the catheter body and configured to discharge fluid received from the source via the conduit.

3. The apparatus of claim 2, wherein the spacing member is porous to fluid dischargeable from the conduit.

4. The apparatus of claim 1, wherein the catheter body defines an aspiration lumen such that fluid can be removed from the body lumen or cavity via the aspiration lumen.

5. The apparatus of claim 1, wherein the spacing member is at least partially transmissive and/or transflective of the light emitted from the light emitter, the spacing member configured such that light emitted from the light emitter can be transmitted radially through the spacing member.

6. The apparatus of claim 1, wherein the spacing member is at least partially transmissive and/or transflective of the light emitted from the light emitter, the spacing member configured such that light emitted from the light emitter can be transmitted radially and axially through the spacing member.

7. The apparatus of claim 1, wherein the spacing member is coupled to the inner body.

8. The apparatus of claim 1, further comprising a light conduit extending through the catheter body from the proximal end to the distal end of the catheter body, the light conduit having a proximal end optically couplable to a source of light and having a distal end optically coupled to the light emitter, the light emitter configured to transmit light from the light source to the light emitter.

9. The apparatus of claim 8, further comprising a light source couplable to the proximal end of the light conduit and configured to generate light at a wavelength in at least one of a visible portion or a near infrared portion of a light spectrum.

10. The apparatus of claim 1, wherein the spacing member includes a wire mesh.

11. The apparatus of claim 1, further comprising an imager disposed at the distal end of the catheter body and configured to image a portion of the body lumen or cavity within which the distal end of the catheter is disposed, the imager couplable to a display on which images of the body lumen or cavity can be displayed.

12. The apparatus of claim 1, wherein the light emitter includes a light scatterer configured to scatter light from the light emitter more uniformly across the spacing member.

13. The apparatus of claim 1, wherein the light emitter is configured to emit light having a power between 1 mW and 500 mW and a wavelength of between 400 nm and 1,000 nm.

14. The apparatus of claim 1, wherein the light emitter is configured to emit light having a power between 100 mW and 200 mW and a wavelength of 532 nm.

15. A method comprising:
disposing a distal end of a catheter in a blood vessel or cavity of a subject adjacent to a region of a wall of the blood vessel or cavity to be treated, the catheter defining a conduit;
transitioning a spacing member from a collapsed configuration to an expanded configuration, the spacing member disposed distally of the distal end of the catheter in the expanded configuration, a diameter of the spacing member in the expanded configuration being equal to or less than an inner dimension of the blood vessel or cavity such that transitioning the spacing member to the expanded configuration does not enlarge the blood vessel or cavity, the spacing member configured to maintain a light emitter approximately centered relative to at least one axis of the spacing member in the expanded configuration; and
emitting light from the light emitter through the blood vessel or cavity and onto the region of the wall of the blood vessel or cavity to be treated, the light emitter disposed on a distal tip of an inner body movably disposed within the conduit of the catheter.

16. The method of claim 15, further comprising:
delivering fluid to the blood vessel or cavity from a source of fluid via the conduit.

17. The method of claim 16, wherein the spacing member is porous to the fluid delivered from the conduit.

18. The method of claim 16, wherein the delivering fluid to the blood vessel or cavity includes diluting blood in the blood vessel or cavity to establish a translucent optical field, and the emitting light includes emitting light at a power and for a duration sufficient to deliver to the diluted blood in the blood vessel or cavity an amount of light energy sufficient to recruit at least one of endothelial progenitor cells or other blood vessel forming cells in the diluted blood.

19. The method of claim 16, wherein the delivering fluid includes diluting blood in the blood vessel or cavity to a ratio of between 2:1 and 1:2 of blood to fluid.

20. The method of claim 16, further comprising:
ceasing to emit light from the light emitter; and
after the ceasing to emit light, ceasing to deliver fluid via the conduit.

21. The method of claim 15, wherein the spacing member is at least partially transmissive and/or transflective of the light emitted from the light emitter, the spacing member configured such that light emitted from the light emitter can be transmitted radially through the spacing member.

22. The method of claim 15, wherein the spacing member is coupled to the inner body.

23. The method of claim 15, wherein the emitting light includes emitting light at a wavelength in at least one of a visible portion or a near infrared portion of a light spectrum.

24. The method of claim 23, wherein the emitting light includes emitting light at a power and for a duration sufficient to deliver to the region of the wall of the blood vessel or cavity an amount of light energy sufficient to recruit cells to endothelialize the region of the wall of the blood vessel or cavity.

25. The method of claim 15, wherein the emitting light includes emitting light at a wavelength between 400 nm and 1,000 nm.

26. The method of claim 15, further comprising:
before the transitioning the spacing member, administering a photosensitive agent into the blood vessel or cavity proximate the distal end of the catheter.

* * * * *